United States Patent
Thurner et al.

(10) Patent No.: US 11,617,768 B2
(45) Date of Patent: Apr. 4, 2023

(54) METHODS FOR OBTAINING MUSCLE DERIVED CELLS

(71) Applicant: INNOVACELL AG, Innsbruck (AT)

(72) Inventors: Marco Thurner, Innsbruck (AT); Eva Margreiter, Innsbruck (AT); Wolfgang Schwaiger, Innsbruck (AT); Faheem Muhammad Asim, Innsbruck (AT); Rainer Marksteiner, Schwaz (AT)

(73) Assignee: INNOVACELL AG, Innsbruck (AT)

( * ) Notice: Subject to any disclaimer, the term of this patent is extended or adjusted under 35 U.S.C. 154(b) by 158 days.

(21) Appl. No.: 16/772,666

(22) PCT Filed: Dec. 14, 2018

(86) PCT No.: PCT/EP2018/085015
§ 371 (c)(1),
(2) Date: Jun. 12, 2020

(87) PCT Pub. No.: WO2019/115790
PCT Pub. Date: Jun. 20, 2019

(65) Prior Publication Data
US 2021/0069255 A1 Mar. 11, 2021

(30) Foreign Application Priority Data
Dec. 14, 2017 (EP) .................................. 17207417

(51) Int. Cl.
*A61K 35/34* (2015.01)
*C12N 5/077* (2010.01)
*A61P 21/00* (2006.01)

(52) U.S. Cl.
CPC ............ *A61K 35/34* (2013.01); *C12N 5/0658* (2013.01); *A61P 21/00* (2018.01); *C12N 2501/599* (2013.01); *C12N 2501/71* (2013.01); *C12N 2509/00* (2013.01); *C12N 2509/10* (2013.01)

(58) Field of Classification Search
CPC .................. A61K 35/34; C12N 5/0658; C12N 2509/00; C12N 2509/10; A61P 21/00
See application file for complete search history.

(56) References Cited

U.S. PATENT DOCUMENTS

| | | |
|---|---|---|
| 2005/0079606 A1 | 4/2005 | Tamaki et al. |
| 2022/0145257 A1 | 5/2022 | Thurner et al. |

FOREIGN PATENT DOCUMENTS

| | | |
|---|---|---|
| EP | 2 206 774 | 7/2010 |
| WO | WO 01/78754 | 10/2001 |
| WO | WO 03/027281 | 4/2003 |
| WO | WO 2007/106200 | 9/2007 |
| WO | WO 2008/153813 | 12/2008 |
| WO | WO 2020/193460 | 10/2020 |

OTHER PUBLICATIONS

Sharifiaghdas, F., Taheri, M., & Moghadasali, R. Isolation of human adult stem cells from muscle biopsy for future treatment of urinary incontinence. Urology Journal, vol. 8, No. 1 (2011) pp. 54-59. (Year: 2011).*
R. Ian Freshney, "Primary Culture." In: Culture of Animal Cell: A Manual of Basic Technique and Specialized Applications. (Hoboken, NJ, John Wiley & Sons, Inc., 2010), pp. 163-186. QH585.2.F74 2010. (Year: 2010).*
R. Ian Freshney, "Primary Culture." In: Culture of Animal Cells: A Manual of Basic Technique and Specialized Applications. (Hoboken, NJ, John Wiley & Sons, Inc. 2010), pp. 163-186. QH585.2.F74 2010. (Year: 2010).*
Abujarour, Ramzey, et al. "Myogenic differentiation of muscular dystrophy-specific induced pluripotent stem cells for use in drug discovery." *Stem cells translational medicine* 3.2 (2014): 149-160.
Gharaibeh, Burhan, et al. "Isolation of a slowly adhering cell fraction containing stem cells from murine skeletal muscle by the preplate technique." *Nature protocols* 3.9 (2008): 1501.
International Search Report and Written Opinion issued in International Application No. PCT/EP2018/085015, dated Feb. 18, 2019.
Lu, A., et al. "Isolation of myogenic progenitor populations from Pax7-deficient skeletal muscle based on adhesion characteristics." *Gene therapy* 15.15 (2008): 1116-1125.
Park, Jung Sik, et al. "Isolation of neural precursor cells from skeletal muscle tissues and their differentiation into neuron-like cells." *Experimental & molecular medicine* 39.4 (2007): 483-490.
Qu, Zhuqing, et al. "Development of approaches to improve cell survival in myoblast transfer therapy." *The Journal of cell biology* 142.5 (1998): 1257-1267.
Rando and Blau. "Primary mouse myoblast purification, characterization, and transplantation for cell-mediated gene therapy." *Journal of Cell Biology* 125.6 (1994): 1275-1287.
Sturgill, Elizabeth R., et al. "Biosynthesis of the major brain gangliosides GD1a and GT1b." *Glycobiology* 22.10 (2012): 1289-1301.
Syverud, Brian C., et al., "Isolation and purification of satellite cells for skeletal muscle tissue engineering." *Journal of regenerative medicine* 3.2. (2014).
Thurner, Marco, et al. "Development of an in vitro potency assay for human skeletal muscle derived cells." *PloS one* 13.3 (2018): e0194561.
Wright, Woodring E., and Jerry W. Shay. "Historical claims and current interpretations of replicative aging." *Nature biotechnology* 20.7 (2002): 682-688.
Krasnopolsky V.I. et al., "Stem cells in the treatment of patients with stress urinary incontinence", Russian Bulletin of an Obstetrician-Gynecologist, 2007, No. 5, 44-47. English Abstract.
Office Action issued in corresponding Japanese Application No. 2020-533052, dated Aug. 9, 2022. With English Translation.
Abrahamsson, Hasse. "Treatment options for patients with severe gastropareris." *Gut* 56.6 (2007): 877-883.

(Continued)

Primary Examiner — Kara D Johnson
(74) Attorney, Agent, or Firm — Parker Highlander PLLC

(57) ABSTRACT

The present invention relates to methods for obtaining skeletal muscle derived cells (SMDC), and the use of SMDCs in a method of preventing and/or treating neuromyopathies and/or myopathies, wherein the neuromyopathy and/or myopathy is incontinence, in particular a urinary and/or an anal or fecal incontinence.

13 Claims, 10 Drawing Sheets

(56) References Cited

OTHER PUBLICATIONS

Al-Ali, S., et al. "Correlation between gross anatomical topography, sectional sheet plastination, microscopic anatomy and endoanal sonography of the anal sphincter complex in human males." *Journal of Anatomy* 215.2 (2009): 212-220.
Bajpai, Vivek K., et al. "Functional vascular smooth miscle cells derived from human induced pluripotent stem cells via mesenchymal stem cell intermediates." *Cardiovascular research* 96.3 (2012): 391-400.
Belkin, Vladimir M., Alexey M. Belkin, and Victor E. Koteliansky. "Human smooth muscle VLA-1 integrin: purification, substrate specificity, localization in aorta, and expression during development." *The Journal of cell biology* 111.5 (1990): 2159-2170.
Bohl, Jaime L., Elie Zakhem, and Khalil N. Bitar. "Successful treatment of passive fecal incontinence in an animal model using engineered biosphincters: a 3-month follow-up study." *Stem cells translational medicine* 6.9 (2017): 1795-1802.
Capetanaki, Yassemi, Derek J. Milner, and G. Weitzer. "Desmin in muscle formation and maintenance: knockouts and consequences." *Cell structure and function* 22.1 (1997): 103-116.
Dash, Biraja C., et al. "Tissue-engineered vascular ring from human iPSC-derived smooth muscle cells." *Stem Cell Reports* 7.1 (2016): 19-28.
Dominici, M et al. "Minimal criteria for defining multipotent mesenchymal stromal cells. The International Society for Cellular Therapy position statement." *Cytotherapy* vol. 8,4 (2006): 315-7.
Espagnoile, Nicolas et al. "CD146 expression on mesenchymal stem cells is associated with their vascular smooth muscle commitment." *Journal of cellular and molecular medicine* vol. 18,1 (2014): 104-14.
Frudinger, A et al. "Autologous skeletal-muscle-derived cell injection for anal incontinence due to obstetric trauma: a 5-year follow-up of an initial study of 10 patients." *Colorectal disease : the official journal of the Association of Coloproctology of Great Britain and Ireland* vol. 17,9 (2015): 794-801.
Frudinger, A et al. "Muscle-derived cell injection to treat anal incontinence due to obstetric trauma: pilot study with 1 year follow-up." *Gut* vol. 59,1 (2010): 55-61.
Frudinger, Andrea et al. "Skeletal muscle-derived cell implantation for the treatment of sphincter-related faecal incontinence," *Stem cell research & therapy* vol. 9,1 233. Sep. 13, 2018.
Goode, Patricia S et al. "Prevalence and correlates of fecal incontinence in community-dwelling older adults." *Journal of the American Geriatrics Society* vol. 53,4 (2005): 629-35.
Huard, J et al. "Muscle-derived cell-mediated ex vivo gene therapy for urological dysfunction." *Gene therapy* vol. 9,23 (2002): 1617-26.
Livanainen, A et al. "Primary structure and expression of a novel human laminin α4 chain." *FEBS letters* vol. 365,2-3 (1995): 183-8.
International Search Report and Written Opinion issued in International Application No. PCT/EP2020/057940, dated Apr. 22, 2020.
Jung, Yunjoon et al. "Concise review: Induced pluripotent stem cells-derived mesenchymal stem cells: progress toward safe clinical products." *Stem cells* (Dayton, Ohio) vol. 30,1 (2012): 42-7.
Krauss, Robert S et al. "Embracing cbange: striated-for-smooth muscle replacement in esophagus development." *Skeletal muscle* vol. 6 27. Aug. 8, 2016.
Lecourt, Séverine et al. "Characterization of distinct mesenchymal-like cell populations from human skeletal muscle in situ and in vitro." *Experimental cell research* vol. 316,15 (2010): 2513-26.
Li, Yanhui et al. "Smooth Muscle Progenitor Cells Derived From Human Pluripotent Stem Cells Induce Histologic Changes in Injured Urethral Sphincter." *Stem cells translational medicine* vol. 5,12 (2016): 1719-1729.
Lu, Shing-Hwa et al. "Characterization of smooth muscle differentiation of purified human skeletal muscle-derived cells." *Journal of cellular and molecular medicine* vol. 15,3 (2011): 587-92.

McHugh, K M. "Molecular analysis of smooth muscle development in the mouse," *Developmental dynamics : an official publication of the American Association of Anatomists* vol. 204,3 (1995): 278-90.
Meng, Jinhong et al. "Contribution of human muscle-derived cells to skeletal muscle regeneration in dystrophic host mice." *PloS one* vol. 6,3 e17454. Mar. 9, 2011.
Meyer, Isuzu, and Holly E Richter. "Impact of fecal incontinence and its treatment on quality of life in women." *Women's health* (London, England) vol. 11,2 (2015): 225-38.
Mimura, Toshiki et al. "Diagnostic evaluation of patients with faecal incontinence at a specialist institution." *Digestive surgery* vol. 21,3 (2004): 235-41.
Niessen, Petra et al. "Smoothelin-a is essential for functional intestinal smooth muscle contractility in mice." *Gastroenterology* vol. 129,5 (2005): 1592-601.
Office Action and Search Report issued in Russian Application No. 2020120580/10(035099), dated Jun. 10, 2022. English Translation.
Park, Won Sun et al., "Functional expression of smooth muscle-specific ion channels in TGF-β(1)-treated human adipose-derived mesenchymal stem cells." *American journal of physiology. Cell physiology* vol. 305,4 (2013): C377-91.
Popescu, L M et al. "Caveolae in smooth muscles: nanocontacts." *Journal of cellular and molecular medicine* vol. 10,4 (2006): 960-90.
Quander, Carline R et al. "Prevalence of and factors associated with fecal incontinence in a large community study of older individuals." *The American journal of gastroenterology* vol. 100,4 (2005): 905-9.
Qu-Petersen, Zhuqing et al. "Identification of a novel po;ulation of muscle stem cells in mice: potential for muscle regeneration." *The Journal of cell biology* vol. 157,5 (2002): 851-64.
Ramkumar, D, and K S Schulze. "The pylorus." *Neurogastroenterology and motility : the official journal of the European Gastrointestinal Motility Society* vol. 17 Suppl 1 (2005): 22-30.
Rao, Satish S C. "Pathophysiology of adult fecal incontinence." *Gastroenterology* vol. 126,1 Suppl 1 (2004): S14-22.
Rochlin, Kate et al. "Myoblast fusion: when it takes more to make one." *Developmental biology* vol. 341,1 (2010): 66-83.
Romaniszyn, Michal, et al. "Implantation of autologous muscle-derived stem cells in treatment of fecal incontinence: results of an experimental pilot study." *Techniques in coproctology* 19.11 (2015): 685-696.
Sanders, K M. "Regulation of smooth muscle excitation and contraction." *Neurogastroenterology and motility : the official journal of the European Gastrointestinal Motility Society* vol. 20 Suppl 1,Suppl 1 (2008): 39-53.
Skuk, Daniel et al. "Intramuscular transplantation of myogenic cells in primates: importance of needle size, cell number, and injection volume." *Cell transplantation* vol. 23,1 (2014): 13-25.
Thurner, Marco et al. "Generation of myogenic progenitor cell-derived smooth muscle cells for sphincter regeneration." *Stem cell research & therapy* vol. 11,1 233. Jun. 12, 2020.
Torrente, Y et al. "Intraarterial injection of muscle-derived CD 34(+)Sca-1(+) stem cells restores dystrophin in mdx mice." *The Journal of cell biology* vol. 152,2 (2001): 335-48.
Trébol, Jacobo et al. "Stem cell therapy for faecal incontinence: Current state and future perspectives." *World journal of stem cells* vol. 10,7 (2018): 82-105.
Vaizey, C J et al. "Primary degeneration of the internal anal sphincter as a cause of passive faecal incontinence." *Lancet* (London, England) vol. 349,9052 (1997): 612-5.
Van de Rijn, M et al. "CD34 expression by gastrointestinal tract stromal tumors." *Human pathology* vol. 25,8 (1994): 766-71.
Van Eys, Guillaume J et al. "Smoothelin in vascular smooth muscle cells." *Trends in cardiovascular medicine* vol. 17,1 (2007): 26-30.
Wang, Gang et al. "Origin and differentiation of vascular smooth muscle cells." *The Journal of physiology* vol. 593,14 (2015): 3013-30.
Wang, Jennifer Y. and Maher A Abbas. "Current management of fecal incontinence." *The Permanente journal* vol. 17,3 (2013): 65-73.
Wang, Jiaxu et al. "Multiple roles of alpha-smooth muscle actin in mechanotransduction." *Experimental cell research* vol. 312,2 (2006): 205-14.

(56) References Cited

OTHER PUBLICATIONS

Wang, Youwei et al. "Safety of mesenchymal stem cells for clinical application." *Stem cell international* vol. 2012 (2012): 652034.
Wörl, Jürgen et al. "Deletion of Pax 7 changes the tunica musculatis of the mouse esophagus from an entirely striated into a mixed phenotype." *Developmental dynamics : an official publication of the American Association of Anatomists* vol. 238,4 (2009): 864-74.
Yin, Hang et al. "Satellite cells and the muscle stem cell niche." *Physiological reviews* vol. 93,1 (2013): 23-67.

\* cited by examiner

METHODS FOR OBTAINING MUSCLE DERIVED CELLS

This application is a national phase application under 35 U.S.C. § 371 of International Application No. PCT/EP2018/085015, filed Dec. 14, 2018, which claims benefit of priority to European Application No. 17207417.1, filed Dec. 14, 2017, the entire contents of each of which are hereby incorporated by reference.

The present invention relates to methods for obtaining skeletal muscle derived cells (SMDC), and the use of SMDCs in a method of improving the neuro-muscular connection and for use in the treatment of a muscle dysfunction, wherein the muscle dysfunction is incontinence, in particular a urinary and/or an anal incontinence.

The ability to maintain continence is fundamental for our well-being as social beings. The loss of anal continence results in physical, physiological and social handicaps. Generally it is thought, that primarily elderly and handicapped people suffer from anal incontinence, however, these symptoms can occur in people of every age. The spectrum of anal incontinence, i.e., the loss of control of the content of the intestine, ranges from minor faeces marks in the underwear to the loss of flatus up to massive episodes of uncontrolled defecation of soft or solid faeces. The reasons for this can be multi-layered and complex. Independently of the extremely impaired life quality for the affected individual, impaired anal continence results in a not to be underestimated cost factor for the public health system. Furthermore, anal incontinence is the second most frequent reason for hospitalisation in nursery homes (more frequently than dementia). One third of the elderly people in nursery homes or hospitals are incontinent for faeces.

Two skeletal muscles are important for the voluntary control of the continence organs: the Musculus sphincter ani externus, and the Musculus puborectalis as a part of the Musculus levator ani. It is likely that the remaining Diaphragma pelvis (M. pubococcygeus, M. ischiococcygeus, M. iliococcygeus) plays a more or less supportive role. The external anal sphincter is supported by the N. pudendus. Both muscles, Musculus sphincter ani externus and the Musculus puborectalis, can maintain a constant tonus directly proportional to the volume/amount of rectal filling, which tonus decreases with start of the defecation process. The constant base line tonus of the M. puborectalis results in a "contortion" of the ano rectal transition towards the symphysis forming an angle of 90° between the anal canal and the rectum. This anorectal angle also contributes to the maintenance of anal continence. A further function of the M. puborectalis is to retain at least partially formed faeces, if the external anal sphincter has been damaged.

Control over flatus or liquid faeces is not possible by M. puborectalis. The anal continence for these faeces types is provided by an interaction of the internal and external anal sphincters. The haemorrhoidal cushions provide for air tight occlusion. In the resting state the anal canal is occluded by the constant tonic activity of the external anal sphincters and the base line resting pressure of the internal anal sphincter. The internal anal sphincter, which is a continuation and enlargement of the circular smooth muscle layer of the colon, provides for about 75-85% of the base line pressure of the closed anal canal. The activity of this smooth muscle component is completely inhibited by a rectal distension, the so called rectal anal inhibitory reflex. This relaxation is accompanied by a reflex contraction of the external anal sphincter and M. puborectalis to prevent defecation.

As mentioned above, current treatment methods primarily aim at the surgical correction of the tearing of the sphincter. This leads to short-term improvement of the symptoms as mentioned above.

Mild forms of anal incontinence can be treated with conservative methods of treatment, which can result in an improvement of the symptoms. However, in more serious cases, the respective surgical intervention results often in a short-term improvement with a small chance of success.

Conservative methods of treatment comprise a dietary change in addition to an increased uptake of fibres as well as in cases with impaired anal sensitivity, the usage of anal tampons and rectal enemas. The intake of loperamid, if necessary, also in combination with bile acid binding substances, reduces the intestinal motility and increases the pressure of the anal sphincter muscle. A new form of therapy utilizes locally applied locally estrogen for postmenopausal women, however, randomised studies are lacking.

However, a distinct number of patients require a surgical intervention: Most frequently, sphincter repair (approximal or overlapping) is applied for the acute treatment of traumatically injuries after giving birth, but also secondarily after injuries of the anal sphincter caused by other circumstances. The short-term prospects are good, long-term results are poor.

For stress urinary incontinence it has been proposed to inject muscle-derived cells into the injured site in order to ameliorate stress urinary incontinence. However, stress urinary incontinence is not comparable to anal incontinence since the causes for the two different diseases are completely different. In addition, the two systems (urinary vs. anal) also do not have similar function. The urinary tract has to provide sufficient control of liquids only. The rectum is capable of controlling solid, fluid as well as gaseous contents. This necessitates completely different sensory requirements. Therefore, the anatomy is quite different between the genitourinary tract and the rectum. For example, while there is an external anal sphincter muscle encircling the rectum, there is no equivalent encircling completely the urethra. Furthermore, dorsal of the urethra hardly any striated muscles can be found in the adult male, while the external anal sphincter of the rectum is a striated muscle that is completely circular.

Myoblasts, the precursors of muscle fibers, are mononucleated muscle cells which differ in many ways from other types of cells. Myoblasts naturally fuse to form post-mitotic multinucleated myotubes which result in the long-term expression and delivery of bioactive proteins. Myoblasts have been used for gene delivery to muscle for muscle-related diseases, such as Duchenne muscular dystrophy, as well as for non-muscle-related diseases, e.g., gene delivery of human adenosine deaminase for the adenosine deaminase deficiency syndrome; gene transfer of human proinsulin for diabetes mellitus; gene transfer for expression of tyrosine hydroxylase for Parkinson's disease; transfer and expression of Factor IX for hemophilia B, delivery of human growth hormone for growth retardation.

The use of myoblasts to treat muscle degeneration, to repair tissue damage or treat disease is disclosed in U.S. Pat. Nos. 5,130,141 and 5,538,722. Also, myoblast transplantation has been employed for the repair of myocardial dysfunction Robinson et al., 1995; Murry et al., 1996; Gojo et al., 1996; Zibaitis et al., 1994.

Myoblasts can also be used in order to repair muscle injuries involved in the maintenance of continence, in particular urinary and/or anal incontinence. Skeletal muscle derived cells comprising myoblasts are known as progenitor cells of skeletal muscles which can undergo differentiation in order to repair muscle injuries in adults.

Several methods are described in the prior art to isolate skeletal muscle derived cells. A distinct method for the isolation of skeletal muscle derived cells applies a pre-plating technique. Thereby, cells are gained from a muscle tissue, and a single cell suspension thereof is transferred consecutively in different cell culture container, also known as pre-plating, to eliminate non-myogenic cells, such as fibroblasts and enrich myogenic cells, such as myoblast. For example, Rando and Blau, 1994 describe such a purification of myoblasts in cell culture (T. A. Rando and H. M. Blau, "Primary mouse myoblast purification, characterization, and transplantation for cell-mediated gene therapy," *J. Cell Biol.,* vol. 125, no. 6, pp. 1275-1287, June 1994). Using multiple pre-plating steps, compared to single pre-plating, improved the purity and survival of myoblasts, which is necessary for the treatment effect in myoblast transfer therapy (Z. Qu, L. Balkir, J. C. T. van Deutekom, P. D. Robbins, R. Pruchnic, and J. Huard, "Development of Approaches to Improve Cell Survival in Myoblast Transfer Therapy," *J. Cell Biol., vol.* 142, no. 5, pp. 1257-1267, September 1998).

The disadvantage of pre-plating technique based methods is that conducting of several pre-plating steps is time consuming. Although cells were passaged multiple times by pre-plating, further re-plating is necessary to reach the desired amount of cells in an effective purity (B. Gharaibeh et al., "Isolation of a slowly adhering cell fraction containing stem cells from murine skeletal muscle by the preplate technique," *Nat. Protoc*, vol. 3, no. 9, p. 1501, August 2008; A. Lu et al., "Isolation of myogenic progenitor populations from Pax7-deficient skeletal muscle based on adhesion characteristics," *Gene Ther., vol.* 15, no. 15, pp. 1116-1125, May 2008). Thus, the extended time in culture and increased number of cell doublings of myoblast during pre- and re-plating may lead to senescence accompanied by growth arrest and even failure to reach the desired amount of cells for myoblast transfer (W. E. Wright and J. W. Shay, "Historical claims and current interpretations of replicative aging," *Nat. Biotechnol., vol.* 20, no. 7, pp. 682-688, July 2002). Furthermore, lack of sensitivity of pre-plating might lead to overall decreased numbers of myoblast even though increased purity might be achieved (B. C. Syverud, J. D. Lee, K. W. VanDusen, and L. M. Larkin, "Isolation and Purification of Satellite Cells for Skeletal Muscle Tissue Engineering," *J. Regen. Med., vol.* 3, no. 2, 2014).

Other methods for isolating myoblasts, such as fluorescence activated cell sorting (FACS) or magnetic activated cell sorting (MACS) seemed promising but due to possible damaging of the cells by applying high voltage laser intensities in FACS as well as concerns about magnetic antibody retention using MACS these methods are not superior choice for myoblast isolation.

In view of these drawbacks of the prior art methods, new methods for the provision of skeletal muscle derived cells (SMDC) are needed.

This object is solved by the subject matter defined in the claims.

The following figures form part of the present specification and are included to further demonstrate certain aspects of the present invention. The invention may be better understood by reference to one or more of these drawings in combination with the detailed description of specific embodiments presented herein.

FIG. 1 shows a phase contrast microscopic picture (100× magnification) of SMDC adhered to standard cell culture flask.

FIG. 2 is a FACS analysis showing the purity and viability of SMDC. The histogram A is a CD56 analysis, and demonstrates that 99.3% cells are positive for CD56. The histogram B shows the 7AAD viability analysis, and demonstrates that 98.77% cells are viable.

Figure 5:
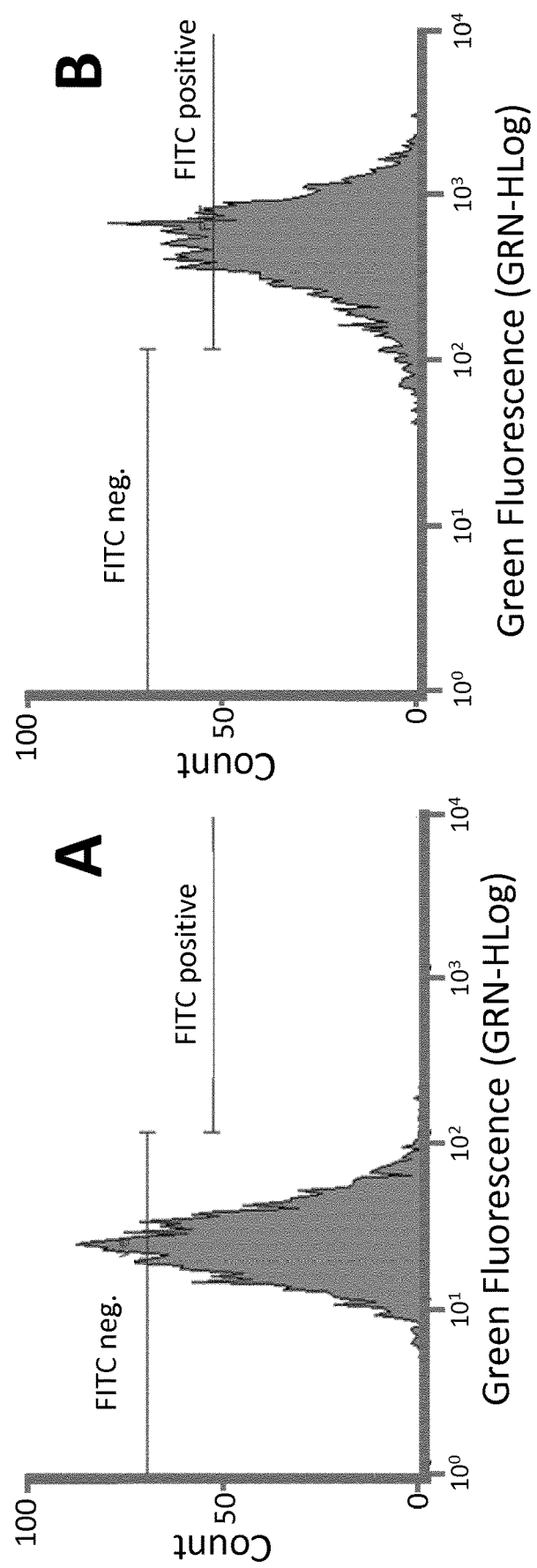

FIG. 5 shows a FACS analysis of A2B5 staining of SMDC. Isotype control staining is shown in histogram A, compared to A2B5 antibody staining, which is shown in histogram B. Histogram B demonstrates that 96% of the cells are positive for A2B5.

Figure 6:
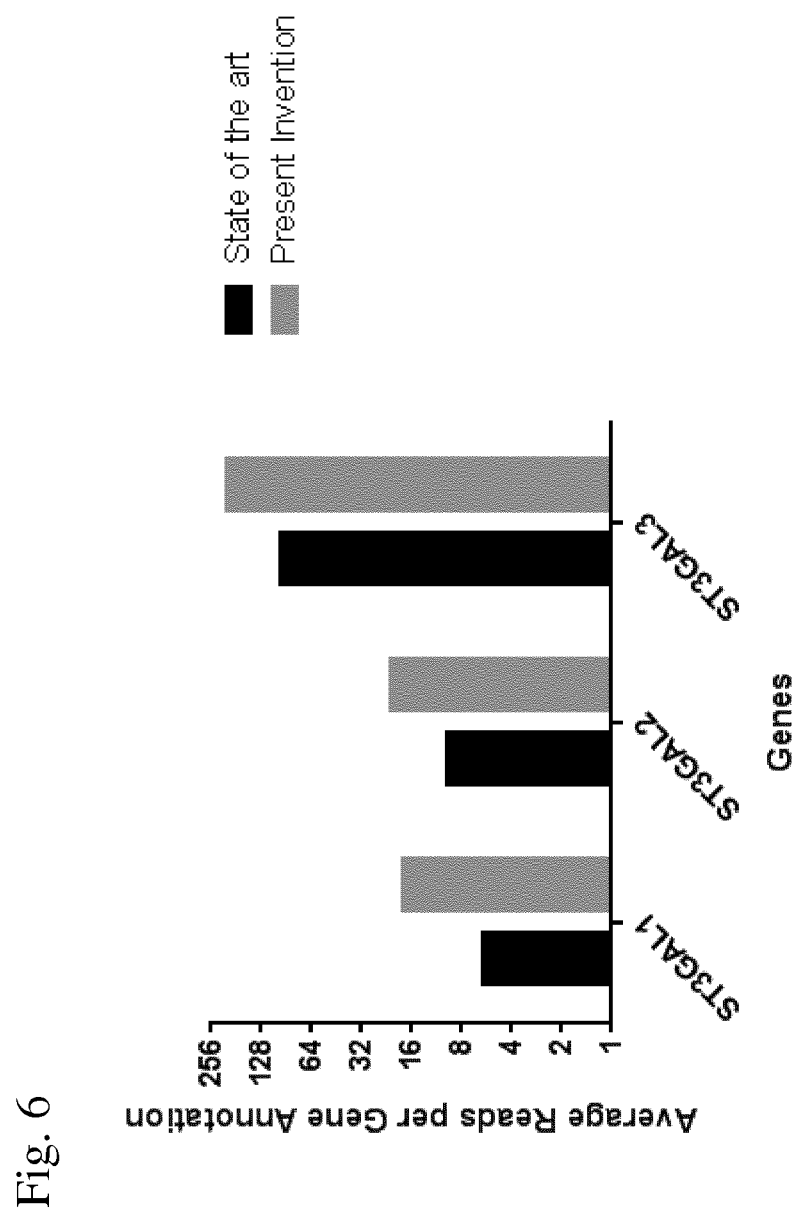

FIG. 6 shows gene expression of A2B5 reactive antigen synthesizing enzymes. Average reads per gene annotation of ST3GAL1, ST3GAL2 and ST3GAL3 suggest a higher expression of these mRNAs in SMDC obtained by the present invention (ST3GAL1: 17.72; ST3GAL2: 20.91; ST3GAL3: 205.89) compared to SMDC commercially available (ST3GAL1: 5.97; ST3GAL2: 9.59; ST3GAL3: 97.81).

Figure 7:
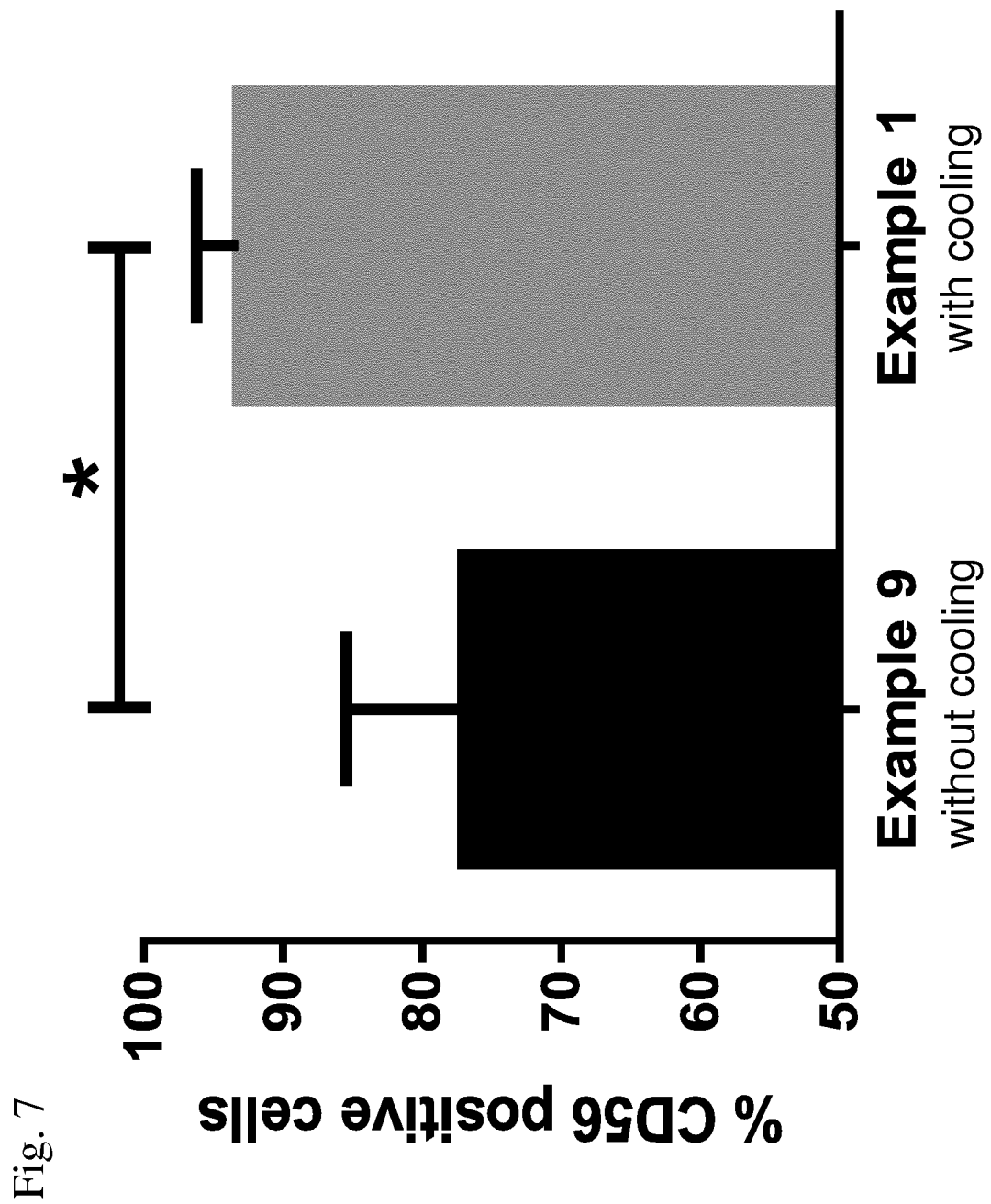

FIG. 7 shows comparison of % CD56 positive cells in cells obtained either by example 1, which means with cooling step, or example 9, which mean without cooling step. Cells obtained by example 1 are demonstrated to contain significantly ($p<0.05$ in a student's t-test; *) higher % CD56 positive cells (mean±SD: 93.28±8.37) compared to cells obtained by example 9 (mean±SD: 77.11±8.37). Data presented as mean±SD of cells derived from muscle biopsies of three individual human donors split in half to perform procedures according to example 1 and 9 on cells from the same donors.

Figure 8:
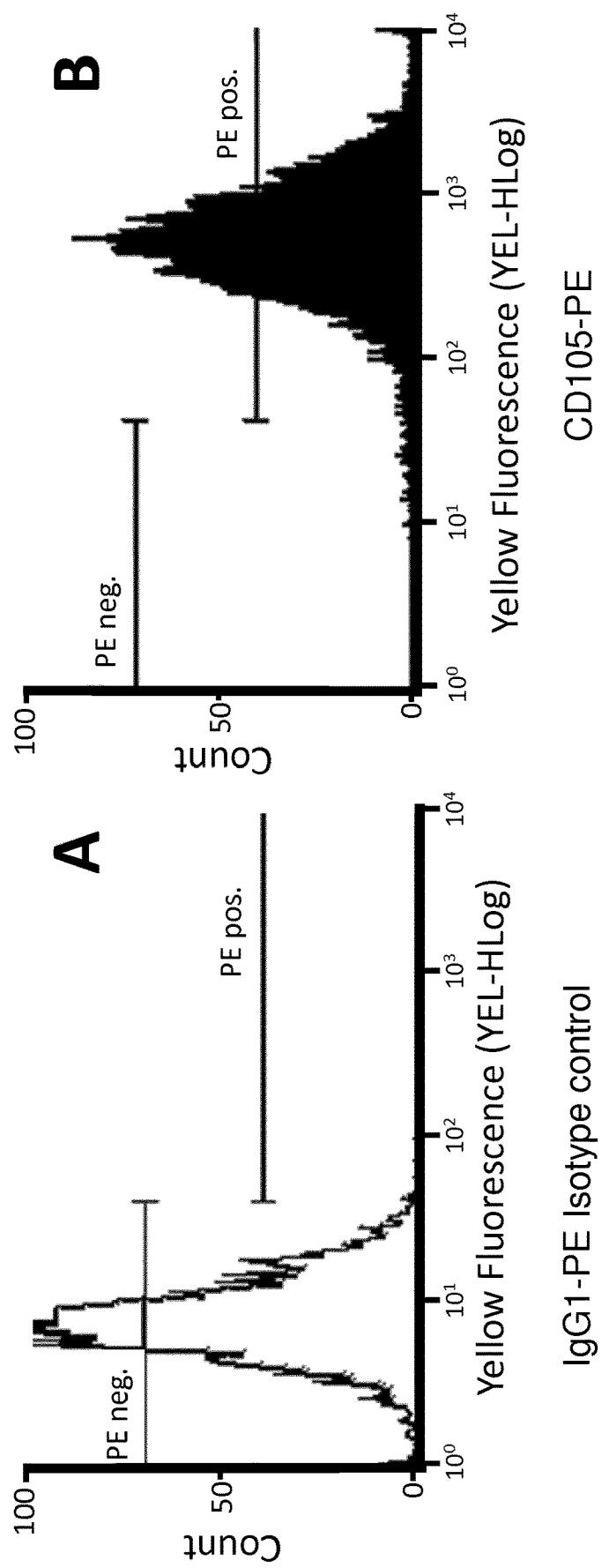

FIG. 8 shows a FACS analysis demonstrating the expression of mesenchymal marker CD105 on SMDC. The histogram B is a CD105 analysis, and demonstrates that 98.69% of SMDC are positive for CD105. The histogram A shows the accurate setting of positivity threshold by demonstrating Isotype control positivity in only 0.31% of SMDC.

Figure 9:
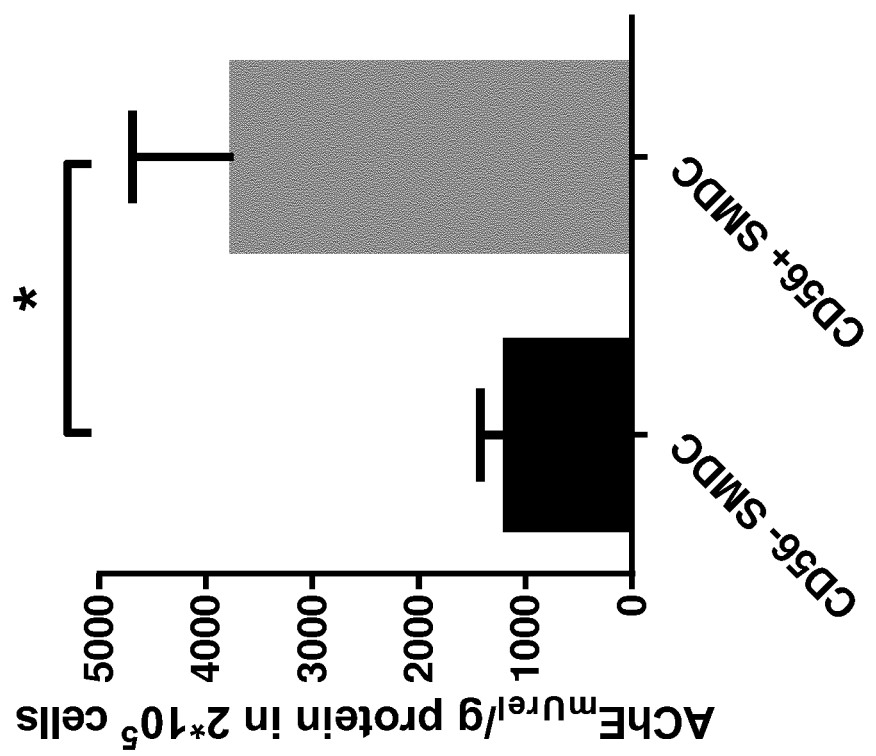

FIG. 9 shows neuromuscular regenerative ability of SMDC according to the present invention by comparing of AChE activity ($mU_{rel}$ per g protein) between CD56+ SMDC (comprising approximately 100% CD56 expressing cells) and CD56− SMDC (comprising approximately 30% CD56 positive cells). AChE activity measurement was performed as described in Example 11. CD56+ SMDC exhibit significantly ($p<0.05$ in a student's t-test; *) higher AChE activity compared to CD56− SMDC. Data presented as mean±SEM of cells derived from muscle biopsies of three individual human donors.

Figure 10:
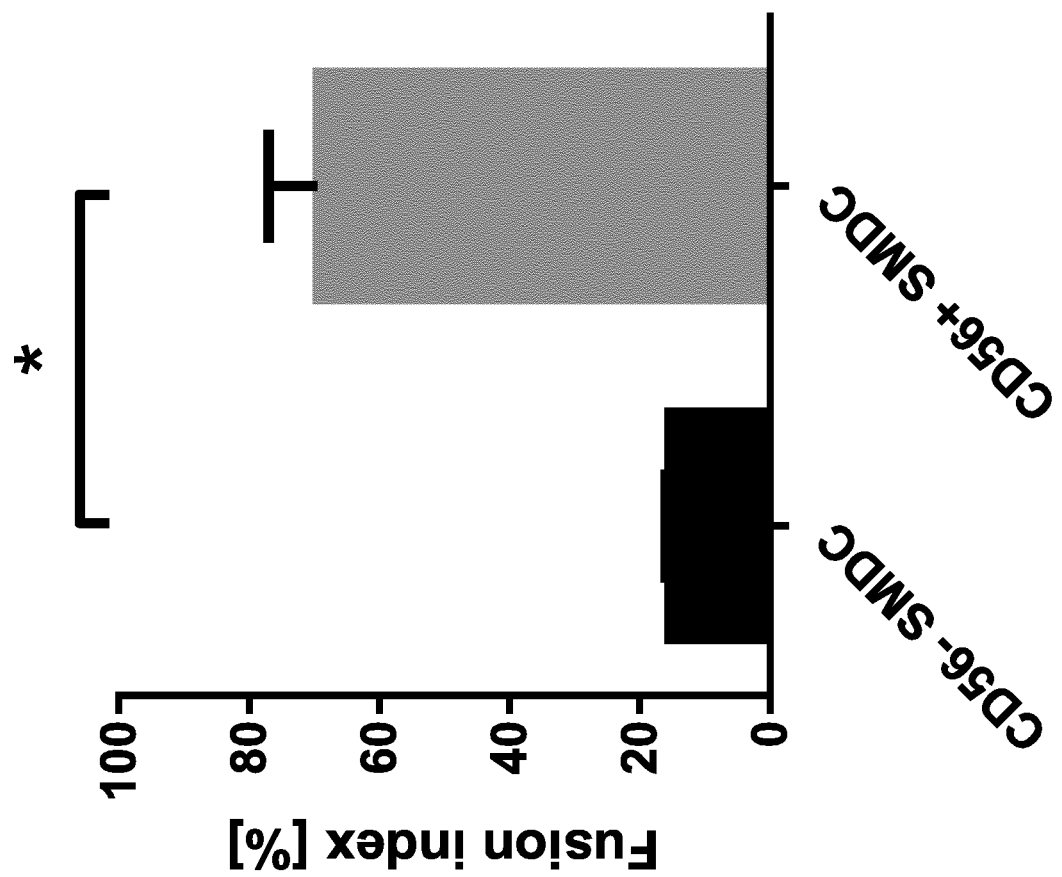

FIG. 10 shows neuromuscular regenerative ability of SMDC according to the present invention by comparing fusion competency (% fusion index) between CD56+ SMDC (comprising approximately 100% CD56 expressing cells) and CD56− SMDC (comprising approximately 30% CD56 positive cells). Fusion competency quantification was performed as described in Example 12. CD56+ SMDC exhibit significantly ($p<0.05$ in a student's t-test; *) higher % fusion index compared to CD56− SMDC. Data presented as mean±SEM of cells derived from muscle biopsies of three individual human donors.

The use of the word "a" or "an" when used in conjunction with the term "comprising" in the claims and/or the specification may mean "one," but it is also consistent with the meaning of "one or more," "at least one," and "one or more than one."

The term "about" means that the value stated, plus or minus 5% of the stated value, or the standard error for measurements of the given value, are contemplated.

The term "anal incontinence," as used herein, refers to any undesired loss of intestine content through the anus, like flatus, liquid or solid faeces. The term comprises all three severity grades: Grade 1=only gaseous, grade 2=liquid and soft feces, grade 3=solid, formed feces.

The term "anal sphincter" or "anal sphincter apparatus," as used herein, refers in particular to the Musculus sphincter ani externus and the Musculus puborectalis as a part of the Musculus levator ani. However it also includes M. pubococcygeus, M. ischiococcygeus, M. iliococcygeus and N. pudendus.

The term "skeletal muscle derived cell" or "SMDC" refers to multinucleated fusion competent cells as e.g. myoblasts, which can be primary cells and/or in vitro cultured cells and alternatively to other cells with myogenic potential (e.g., from liposuctioned tissue or other stem cell harbouring tissues such as bone marrow). The term also comprises cells derived from adipose which can be isolated and used for culturing of skeletal muscle cells. The term "skeletal muscle derived cell" or "SMDC" also refers to a cell population isolated from muscle tissue. Generally, such a cell population comprises further cells not having a myogenic potential. Such cells are called "non-myogenic cells" or "skeletal muscle derived non-myogenic cells" herein and are preferably CD56 negative and/or desmin negative. Thus, the term "skeletal muscle derived cell" or "SMDC" as used herein refers preferably to a cell population comprising at least 30, 40, 50, 60, 70, 80, 90, 95, 98 or 100% multinucleated fusion competent cells.

The term "penetration," as used herein, refers to a process of introducing an injection device, for instance a needle into a body tissue without affecting the injection process yet.

The term "injection," as used herein, refers to the expulsion of an injection solution comprising above mentioned cells out of an injection device into a specific site within the human body, in particular into or adjacent to muscle-tissue providing for anal continence. The injection process can be, but is not limited to, static, i.e., the injection device remains at the position reached. Alternatively, the injection process is dynamic. For instance, in some embodiments of the present invention the injection occurs simultaneously with the retraction of the injection device from the site of injection.

The term "injection site," as used herein, refers to a site within the human body, such as close to or being muscle-tissue providing for anal continence, at which the injection process is initiated. The injection site needs not to be identical with the site where the injection process ends.

The term "injection device," as used herein, refers to any device suitable for penetrating human tissue in order to reach an injection site of interest and capable of delivering solutions, in particular solutions comprising muscle-derived cells to the injection site of interest.

The term "faeces incontinence," as used herein, refers only to the undesired loss of liquid or formed faeces through the anus.

The term "passive incontinence," as used herein, refers to a lack of sensory recognition of loss of faeces. This comprises low anal base line pressure values and a lacking sensoric ability of the anal and rectal mucosa.

"Imperative defecation" or "imperative urgency," as used herein, refers to the lacking ability of a person to delay defecation for more than five minutes. Such a patient has to go to the toilette immediately.

The term "CD56+" or "CD56 positive" as used herein refers to a cell expressing the cell marker CD56. The terms "CD56+" or "CD56 positive" can also be used for a cell population comprising different cell types, if preferably at least 50, 60, 70, 80, 90, 95, 98 or 99 percent of the cell population express the cell marker CD56.

The term "CD56−" or "CD56 negative" as used herein refers to a cell not expressing the cell marker CD56. The terms "CD56−" or "CD56 negative" can also be used for a cell population comprising different cell types, if preferably at most 49, 40, 30, 20, 10, 5, 4, 3, 2, 1 or 0 percent of the cell population express the cell marker CD56.

The term "A2B5+" or "A2B5 positive" as used herein refers to a cell expressing the cell marker A2B5. The terms "A2B5+" or "A2B5 positive" can also be used for a cell population comprising different cell types, if preferably at least 50, 60, 70, 80, 90, 95, 98 or 99 percent of the cell population express the cell marker A2B5.

The term "A2B5−" or "A2B5 negative" as used herein refers to a cell not expressing the cell marker A2B5. The terms "A2B5−" or "A2B5 negative" can also be used for a cell population comprising different cell types, if preferably at most 49, 40, 30, 20, 10, 5, 4, 3, 2, 1 or 0 percent of the cell population express the cell marker A2B5.

The term "desmin positive" as used herein refers to a cell expressing the cell marker desmin. The term "desmin positive" can also be used for a cell population comprising different cell types, if preferably at least 50, 60, 70, 80, 90, 95, 98 or 99 percent of the cell population express the cell marker desmin.

The term "desmin negative" as used herein refers to a cell not expressing the cell marker desmin. The term "desmin negative" can also be used for a cell population comprising different cell types, if preferably at most 49, 40, 30, 20, 10, 5, 4, 3, 2, 1 or 0 percent of the cell population express the cell marker desmin.

The term "CD105+" or "CD105 positive" as used herein refers to a cell expressing the cell marker CD105. The terms "CD105+" or "CD105 positive" can also be used for a cell population comprising different cell types, if preferably at least 50, 60, 70, 80, 90, 95, 98 or 99 percent of the cell population express the cell marker CD105.

The term "CD105−" or "CD105 negative" as used herein refers to a cell not expressing the cell marker CD105. The terms "CD105−" or "CD105 negative" can also be used for a cell population comprising different cell types, if preferably at most 49, 40, 30, 20, 10, 5, 4, 3, 2, 1 or 0 percent of the cell population express the cell marker CD105.

The term "differentiation media" as used herein refers to cell culture media which induce fusion in multinucleated fusion competent cells or myogenic cells as e.g. myoblasts. However, said term refers also to cell culture medium not comprising any substances necessary for the induction of fusion, in case the multinucleated fusion competent cells or myogenic cells are able to fuse without a respective induction.

The term "cell growth medium" as used herein refers to any medium suitable for the incubation of mammalian cells such as SMDC, which allows the attachment of said mammalian cells on the surface of an incubation container.

In accordance with the present invention, methods for obtaining skeletal muscle derived cells (SMDC) are provided.

A first subject-matter of the present invention is directed to a method for obtaining skeletal muscle derived cells (SMDC), the method comprises the steps of: (a) cooling of a sample obtained from skeletal muscle tissue in a buffer; (b) processing and cooling of the sample; (c) resuspending the sample of step (b) in medium with serum comprising at least one enzyme and heating up to 38° C. for 1 to 20 hours; pelleting the sample and (d) resuspending the pellet of the sample of step (c) to provide a single cell suspension from the sample of step (c), thereby obtaining SMDC.

The inventors found that conducting of the method of the present invention advantageously allows obtaining and enriching of SMDC, exhibiting high myogenic capacity, without the necessity of conducting pre-plating steps. These enriched SMDC are highly pure for myogenic markers such as CD56 and desmin, indicating increased myogenic potential as assayed for example by a suitable potency assay. Furthermore, enriching the SMDC before initial plating is advantageous as the cells have to undergo less sub cultivation, thus leading to lower amount of senescent cells and high viability due to the present invention. Additionally, the present invention generates cells not only expressing myogenic markers such as CD56 and desmin, but also markers of neuronal precursor cells such as A2B5 suggesting also potential for neuro-muscular support. In fact, SMDC obtained by the present invention are different from state of the art cells in their gene expression of A2B5 reactive antigen synthesizing enzymes ST3GAL1 ST3GAL2 and ST3GAL3, necessary for neuromuscular support of A2B5 reactive antigens. Summarizing, enriched SMDC obtained by the present invention demonstrate high purity and viability thus are suggested to have high clinical efficacy in supporting the neuro-muscular connection as well as regenerating muscle weakness especially in conditions as urinary and/or faecal incontinence.

In a preferred embodiment of the present invention, step (a) comprises conducting a muscle biopsy.

Such muscle biopsy serving as the source of muscle-derived cells can be obtained from the muscle at the site of injury or from another area that may be more easily accessible to the clinical surgeon. The site of the biopsy is not restricted to a distinct skeletal muscle, and may be such as from the upper arm. The size of the biopsy may comprise approximately 1 cm×1 cm×1 cm or bigger.

For using myoblasts in the treatment of muscle injuries for example for the treatment of incontinence said myoblasts are preferably isolated from a skeletal muscle biopsy of the subject to be treated.

In a further preferred embodiment, step (a) is conducted at a temperature lower than 16° C., preferably at a temperature range from 1 to 16° C., preferably 4 to 10° C., in particular preferred at 7° C.; and for a time in the range of up to 96 hours.

Accordingly, it is preferred that the method of the present invention is conducted in step (a) at a temperature range of 1 to 16° C. or at any temperature in between this range, such as at 2, 3, 4, 5, 6, 7, 8, 9, 10, 11, 12, 13, 14, 15° C., or any intermediate temperature within this range. In a further preferred embodiment of the present invention, the temperature range is from 6 to 8° C. In a further preferred embodiment the temperature range is below 4° C., preferably in the range from 1 to 3° C.

Further, it is preferred that the method of the present invention in step (a) is conducted at a time in the range of up to 96 hours, or any time within this range, such as 12 to 96 hours, 12 to 72 hours, 12 to 48 hours, 24 to 96 hours, 24 to 72 hours, 24 to 48 hours, or any other intermediate range.

Preferably, step (b) comprises the use of scissors, scalpel, tweezers, filter, or ball mill and a centrifuge. However, it is apparent for a person skilled in the art that any other means which allow the mincing or shredding of the skeletal muscle tissue is encompassed and in accordance with the present invention.

In a further preferred embodiment, step (b) is conducted at a temperature in the range of 1 to 16° C. or at any temperature in between this range, such as at 2, 3, 4, 5, 6, 7, 8, 9, 10, 11, 12, 13, 14, 15° C., or any intermediate temperature within this range. In a further preferred embodiment of the present invention step (b) is conducted at a temperature in the range from 4 to 8° C., in particular preferred 4° C. In a further preferred embodiment the temperature range is below 4° C., preferably in the range from 1 to 3° C.

Further preferred, step (b) of the present invention is conducted for a distinct time range, such as 2 to 48 hours, or any time within this range, such as 2 to 36 hours, 2 to 24 hours, or any other intermediate range.

Accordingly, it is foreseen that step (b) of the method of the present invention is conducted by processing of the skeletal muscle tissue and cooling for the distinct period of time of the processed skeletal muscle tissue. In a preferred embodiment of the invention, it is foreseen that the cooling of the sample is conducted after the processing step. The inventors found out that the cooling of the processed sample is advantageous since this leads to a crucial diminishing of non-myogenic cells, such as fibroblasts, which is achieved since non-myogenic cells, such as fibroblasts, are temperature-sensitive, because of higher metabolic activity than quiescent myogenic cells. Due to this characteristic non-myogenic cells, such as fibroblasts, are dying due in the cold temperature condition. As a consequence of this, the cooling in step (b) of the method of the present invention provides an enrichment of myogenic cells. This enrichment is achieved without the necessity of conducting any pre-plating steps. Therefore, the method of the present invention provides a good enrichment and purification of myogenic cells without the necessity of conducting time and cost consuming steps.

The importance of the cooling step is in particular demonstrated in form of comparative data shown in the examples below. Therein it is shown that the amount of CD56 positive cells is significantly elevated. CD56 positive cells represent a marker that demonstrates the purity of the obtained SMDCs. Therefore, the method of the present invention represents a method which allows obtaining SMDCs in a higher quantity as well as higher quality compared to the methods of the prior art which do not conduct a cooling step as it is foreseen in the method of the present invention.

CD56 also known as neural cell adhesion molecule (NCAM) is a myogenic commitment marker expressed in skeletal muscle myoblasts in vitro (Belles-Isles et al., 1993) and smooth muscle tissue in vivo (Romanska et al., 1996). CD56 is present in fusion competent desmin+SMDC. CD56 in particular has been demonstrated to mark a SMDC population that is able to form multinucleated myotubes and express higher enzymatic acetylcholinesterase (AChE) activity than CD56 negative SMDC (Thurner et al., 2018). High AChE activity of SMDC used to treat fecal incontinent patients in fact has been linked to high treatment success in terms of reduction of fecal incontinence symptoms (Thurner et al., 2018). Thus, SMDC highly pure for CD56 and thus high in AChE activity are desired for successful treatment of patients with neuromyopathies and/or myopathies such as fecal incontinence. The present invention provides a method to isolate SMDC highly pure for CD56 and with high AChE activity.

Preferably, it is foreseen that step (c) comprises conducting the enzymatically treating with a solution comprising any one or more selected from the group consisting of trypsin, papain, elastase, hyaluronidase, collagenase, deoxyribonuclease, and DNAse. In a preferred embodiment step (c) foresees the use of collagenase.

In accordance with the present invention, it is preferably foreseen that resuspending in step (c) comprises the centrifugation of the sample of step (b), discarding the supernatant and resuspending of the cell pellet in a medium with serum comprising at least one enzyme. Further, in a preferred embodiment of the present invention it is also preferred that one or more washing steps are conducted with the cells in step (c), including vortexing of the cells in a suitable solution, such as a buffer. According to the invention, the resuspended sample of step (b) in the medium with serum comprising at least one enzyme is centrifuged after the incubation time to pellet the cells of the sample and to discard the enzyme containing supernatant.

In a particular preferred embodiment of the invention the enzyme in step (c) is trypsin.

In a further preferred embodiment of the present invention, step (c) is conducted at a temperature in the range of 25 to 38° C., preferably 36 to 38° C., in particular preferred at 37° C.

Preferably, step (d) comprises preferably a method selected from at least one of FACS sorting, centrifugation, electrokinetic sorting, acoustophoresis sorting, bead-based cell sorting, and optical sorting.

Methods for obtaining single cell suspension are well known in the art. One example for a suitable enrichment method is magnetic-activated cell sorting (MACS®). The MACS method allows cells to be separated by incubating the cells with particles (http://en.wikipedia.org/wiki/Magnetic_nanoparticles) coated with antibodies against a particular surface antigen. Subsequently, the incubated cells are transferred on a column placed in a magnetic field. In this step, the cells which express the antigen and are therefore attached to the nanoparticles stay on the column, while other cells not expressing the antigen flow through the column. By this method, the cells can be separated positively and/or negatively with respect to the particular antigen(s). Another example for a suitable enrichment method is fluorescence-activated cell sorting (FACS®) as e.g. described in Webster et al. (Exp Cell Res. 1988 January; 174(1):252-65).

In a further preferred embodiment of the present invention, a further optional step (e) is conducted after step (d) including incubating of the single cell suspension obtained in step (d), wherein the incubation in step (e) is preferably conducted at a temperature in the range of 25 to 38° C., preferably 36 to 38° C., in particular preferred at 37° C., thereby obtaining adherent SMDC.

This further optional incubation step allows to let the cells grow to achieve a higher amount of SMDC. A person skilled in the art will adjust the culture conditions, such as medium and temperature, accordingly to gain a maximum amount of SMDC.

Further preferred, it is foreseen that after step (e) optionally a further step (f) is conducted comprising discarding of non-adherent cells of step (e), wherein step (f) is preferably conducted after at least 6 hours to 4 days.

According to the present invention, this optional step allows preferably that non-myogenic cells or cells which are floating in the culture container, such as dead cells, are discarded. Thereby the desired adherent cells are further enriched. A person skilled in the art will conduct the optional step (f) at a suitable time within the preferred range of 6 hours to 3 days depending on the actual need to perform such a step. Whether such an optional step (f) is indeed necessary, can be defined for example with observation of the cells under a microscope and determine the amount of non-adherent cells in the cell culture.

In a further preferred embodiment of the present invention, after step (f) optionally a further step (g) is conducted of propagating of the adherent cells of step (e), the propagating in step (h) comprises culturing of the adherent cells for 1 to 5 passages to 70 to 80% confluency.

In accordance with the present invention, a person skilled in the art is able to determine the necessary duration and amount of passages to achieve the desired confluency of 70 to 80%.

A second subject-matter of the present invention is directed to SMDC, wherein the SMDC comprise at least 60% CD56 positive and 60% A2B5 positive cells.

In a further preferred embodiment of the invention, the SMDC are CD105 positive, which means that the SMDC express CD105 on their cell surface.

In a preferred embodiment of the invention, at least 60%, 70%, 80%, 90%, 95% or 98% or any intermediate range between the mentioned values of the SMDC are CD105 positive, which means that the SMDC express CD105 on their cell surface.

CD105 is also known as Endoglin. It is a type I integral membrane homodimer protein with subunits of 90 kD found on vascular endothelial cells and syncytiotrophoblasts of placenta. CD105 is weakly expressed on stromal fibroblasts. It is also expressed on activated monocytes and tissue macrophages. Expression of CD105 is increased on activated endothelium in tissues undergoing angiogenesis, such as in tumors, or in cases of wound healing or dermal inflammation. CD105 is a component of the TGF-β receptor system in human umbilical vein endothelial cells and binds TGF-β1 and β with high affinity but does not bind to TGF-β2. TGF-β receptors have been demonstrated to be required for skeletal muscle differentiation. In fact, TGF-β receptor was shown to be necessary for increase in myogenin, a skeletal muscle differentiation factor, and fusion competency of myoblasts. Thus, CD105 positive cells may be preferred for SMDC and SMDC obtained by the methods disclosed in the present invention.

In a further preferred embodiment of the invention, the SMDC are desmin positive, which means that the SMDC express desmin on their cell surface.

In a preferred embodiment of the invention, at least 60%, 70%, 80%, 90%, 95% or 98% or any intermediate range between the mentioned values of the SMDC are desmin positive, which means that the SMDC express desmin on their cell surface.

In a further preferred embodiment of the invention, the SMDC are Pax7 positive, which means that the SMDC express Pax7 on their cell surface.

In a further preferred embodiment of the invention, the SMDC are Myf5 positive, which means that the SMDC express Myf5 on their cell surface.

A2B5 reactive antigens belong to the family of c-series gangliosides, a family of glycolipids that are most abundant in the nervous system where they exhibit functions such as cell-cell adhesion and recognition as well as signal transduction. Loss of gangliosides leads to severe neurological defects, such as regenerative defects of motor neurons in c-series gangliosides deficient mice (R. K. Yu, Y.-T. Tsai, T.

Ariga, and M. Yanagisawa, "Structures, biosynthesis, and functions of gangliosides—An overview," *J. Oleo Sci.*, vol. 60, no. 10, pp. 537-544, 2011). Also at the neuro-muscular junction (NMJ) a high amount of gangliosides was found. Treating NMJ with anti-ganglioside antibodies led to severe defect in the NMJ, thus supporting the idea that gangliosides are necessary at the NMJ (J. J. Plomp and H. J. Willison, "Pathophysiological actions of neuropathy-related anti-ganglioside antibodies at the neuromuscular junction," *J. Physiol*, vol. 587, no. Pt 16, pp. 3979-3999, August 2009). Furthermore gangliosides especially mark stem cells, considered to have regenerative potential (R. K. Yu, Y.-T. Tsai, T. Ariga, and M. Yanagisawa, "Structures, biosynthesis, and functions of gangliosides—An overview," *J. Oleo Sci*, vol. 60, no. 10, pp. 537-544, 2011). A2B5 reactive gangliosides are synthesized by sialyltransferases. Among them those with highest in vitro glycosphingolipid acceptor activity highly expressed in the brain are ST3GAL1 and ST3GAL2 (E. R. Sturgill et al., "Biosynthesis of the major brain gangliosides GD1a and GT1b," *Glycobiology*, vol. 22, no. 10, pp. 1289-1301, October 2012). mRNA of both ST3GAL1 and ST3GAL2 is expressed in SMDC obtained by the present invention and expressed in greater amount compared to commercially available SMDC. Taken together SMDC with myogenic regenerative capability also expressing A2B5 reactive antigens might not solely regenerate skeletal muscle but also provide neuro-muscular support especially at the newly forming neuromuscular junction during muscle regeneration.

The SMDC, which can be used for the treatment of a muscle dysfunction, in particular for the treatment of incontinence such as urinary and/or anal incontinence, exhibit preferably a characteristic expression pattern. Preferably, more than about 60%, 70%, 80%, 90%, 95% or 98% of said SMDC express CD56 and A2B5. Preferably, said SMDC do not express CD34, Sca-1 and MyoD. Thereby, the term "do not express" means that preferably less than 40%, 30%, 20%, 10%, 5% or 2% of the SMDC express said markers. The expression pattern of SMDC as described above can be used to determine the myogenicity index of the cell culture without the requirement of differentiation. Thus, said expression pattern of SMDC can be to verify, whether skeletal muscle derived cells can be used for the treatment of a muscle dysfunction, in particular for the treatment of incontinence such as urinary and/or anal incontinence.

A further subject-matter of the present invention is directed to SMDC obtained according to a method of the present invention.

In accordance with the present invention, the SMDC obtained with the method of the present invention can clearly be distinguished from cells of the prior art in view of the distinct expression of the A2B5 marker and/or A2B5 marker reactive antigen synthesizing enzymes. Since A2B5 reactive gangliosides are synthesized by sialyltransferases, these sialyltransferases may thus serve as an indirect marker for the expression of A2B5. Among the three important sialyltransferases ST3GAL1, ST3GAL2 and ST3GAL3, those with highest in vitro glycosphingolipid acceptor activity highly expressed in the brain are ST3GAL1 and ST3GAL2 (E. R. Sturgill et al., "Biosynthesis of the major brain gangliosides GD1a and GT1b," *Glycobiology*, vol. 22, no. 10, pp. 1289-1301, October 2012). The detection of the expression of ST3GAL1 and ST3GAL2 allows the indirect proof of the expression of A2B5. Therefore, the new method of the present invention allows obtaining SMDC which are different compared to SMDC obtained with methods known in the art.

In a further preferred embodiment of the present invention, the SMDC and the SMDC obtained by the method according to the present invention are characterized by the expression of distinct markers. It is foreseen according to the present invention that the SMDC are characterized by the positive expression of one, two, three, four or five of the markers CD56, A2B5, CD105, desmin, Myf5, and Pax7. Further preferred, it is foreseen that the SMDC and SMDC obtained by the method according to the present invention, are characterized by the expression of distinct marker combinations selected from the positive expression of at least one or more of the markers selected from CD56, A2B5, CD105, Myf5, and Pax7, and the negative expression of at least one or more markers selected from CD34, and MyoD. Preferably, at least 60%, 70%, 80%, 90%, 95% or 98% or any intermediate range between the mentioned values of the SMDC are positive for any one or more of CD56, A2B5, CD105, Myf5, and Pax7, which means that the SMDC express of CD56, A2B5, CD105, Myf5, and/or Pax7 on their cell surface. Further preferred, at most 59%, 50%, 40%, 30%, 20%, 10%, 5%, 4%, 3%, 2%, 1% or 0% of the cell population express any one of CD34 and/or MyoD.

In a particular preferred embodiment of the invention, the SMDC and SMDC obtained by the method according to the present invention are characterized by the positive expression of CD56, A2B5, CD105, Myf5, Pax7, and the negative expression of CD34 and MyoD.

A further subject-matter of the present invention is directed to SMDC obtained according to a method of the present invention for use as a pharmaceutical composition.

In accordance with the present invention, SMDC obtained according to a method of the present invention can be used as active ingredient within a pharmaceutical composition.

A further subject-matter of the present invention is directed to SMDC obtained according to a method of the present invention for use in a method of improving of the neuro-muscular connection.

Preferably, the SMDCs according to the present invention are for use in a method of improving preventing and/or treating of neuromyopathies and/or myopathies. Preferably, the SMDC are for use in a method of preventing and/or treating neuromyopathies and/or myopathies such as fecal incontinence and/or urinary incontinence.

In accordance with the present invention SMDC may be used in a method which preferably foresees that the SMDC are injected in a subject suffering from incontinence. In general, injecting SMDC into a given tissue or site of injury comprises a therapeutically effective amount of cells in solution or suspension, preferably of about $1 \times 10^5$ to about $6 \times 10^6$ cells per 100 µl of injection solution. The injection solution is a physiologically acceptable medium, with or without autologous serum. Physiological acceptable medium can be by way of non-limiting example physiological saline or a phosphate buffered solution.

Finally, a further subject-matter of the present invention is directed to SMDC obtained according to a method of the present invention for use in a method of treating a muscle dysfunction, wherein the muscle dysfunction is incontinence, in particular a urinary and/or an anal incontinence.

In principle, any type of anal incontinence can be treated, as the strengthening of the anal muscle systems provides for a better control of the rectal filling. However, anal incontinence that results from perineal rupture, especially if the anal sphincter system and/or if the M. puborectalis is damaged and injured, is treated. Such perineal rupture can result from a broad variety of causes as outlined above. However, the cause of such perineal rupture is not in limiting for the application of the methods and SMDC of the present invention. Patients may be treated with the methods and SMDC of the present invention if they suffer from a perineal rupture of the third or fourth grade. This applies in particular to women which suffer from such perineal rupture after forceps delivery, give birth for the first time, deliver a child of a weight over 4 kg, or suffer from a consequence due to position anomalies of the child before birth. The methods and SMDC of the present invention can also be applied after injury of the anal sphincter system and/or M. puborectalis due to surgical procedures. Additionally, the methods and SMDC of the present invention can also be applied if there is only transient incontinence. Such treatment prevents development of full anal incontinence. Further anal incontinence disease states to be treated with the methods and SMDC of the present invention are passive incontinence, faeces incontinence and imperative defecation.

It should be understood that the methods and SMDC according to the present invention cannot only be used to treat patients already suffering from anal incontinence, i.e., showing symptoms of anal incontinence, but may be applied to subjects not yet suffering from anal incontinence, but with increased risk of doing so, for example, in cases where the rectal musculature suffered damage from surgery, birth, accidents and so forth. Another example would be cases where the rectal musculature became thinner than in a healthy individual or where it degenerated due to other reasons. The methods of the present invention can provide a suitable prophylaxis to prevent onset of anal incontinence.

The SMDC for use in the treatment or prophylaxis of incontinence are preferably homologous to the recipient.

In a more preferred embodiment said SMDC are autologous or heterologous to the recipient. Said SMDC may e.g. be obtained by a biopsy of the biceps of the recipient. Autologous SMDC reduce or minimize the risk of allergic reactions, after the SMDC have been injected into the recipient. Preferably, the SMDC are multinucleated fusion competent cells or myogenic cells such as myoblasts. More preferably, the said SMDC are human cells.

Therefore, the present invention also provides a simple prophylaxis approach or treatment method for women and men with urinary and/or anal incontinence or in risk of developing urinary and/or anal incontinence by using autologous skeletal muscle-derived cells to enhance their urinary and/or anal sphincters. Such muscle-derived cell therapy allows repair and improvement of damaged urinary and anal sphincter. In accordance with the present invention the treatment comprises a needle aspiration to obtain muscle-derived cells, for example, and a brief follow-up treatment to inject cultured and prepared cells into the patient. Also according to the present invention, autologous skeletal muscle derived cells (SMDC) harvested from and cultured for a specific urinary and/or anal incontinence patient can be employed as a non-allergenic agent to bulk up the urinary and/or rectum wall, thereby enhancing coaptation and improving the urinary and/or anal sphincter muscle. In this aspect of the invention, simple autologous muscle cell transplantation is performed, as discussed above.

In accordance with the present invention, autologous skeletal muscle-derived cells administered directly into the urinary sphincter and/or anal sphincter, exhibit long-term survival. Thus, autologous myoblast injection results in safe and non-immunogenic long-term survival of myofibers in the urinary and/or anal sphincter.

In a particular embodiment according to the invention, about 50 to about 200 µl of a skeletal muscle-derived cell suspension (with a concentration of about $1 \times 10^5$ to about $6 \times 10^6$ cells per 100 µl of injection solution) are injected into the urinary sphincter. The injection device can be connected to a container containing the cell suspension to be injected. For the treatment of anal incontinence preferably about 50 µl to about 1 ml, more preferably about 0.5 ml of a skeletal muscle-derived cell suspension (with a concentration of about $1 \times 10^5$ to about $6 \times 10^6$ cells per 100 µl) are injected into the external anal sphincter. The injection device can be connected to a container containing the cell suspension to be injected.

In another embodiment, the injection step may comprise several individual injections, such as about 20 to about 40 injections of skeletal muscle-derived cell suspension, wherein in each injection about 50 to about 500 µl of a skeletal muscle-derived cell suspension are injected and wherein each injection is applied to another region of the anal sphincter. However, these parameters have to be considered as being merely exemplarily and the skilled artisan will readily be able to adapt these procedures to the treatment requirements for each individual patient.

In another embodiment of the present invention, the movement of the injection device towards the urinary and/or anal sphincter is monitored by sonography and/or EMG (electromyography) means. In a particular embodiment, a transrectal probe is introduced and the position of the transrectal probe is adjusted optimally for the treatment of the urinary and/or anal sphincter with the methods according to the invention. In another particular embodiment, the skeletal muscle-derived cells are implanted in the area surrounding the urinary and/or anal sphincter defect and/or especially in the area of the urinary and/or anal sphincter defect. The patient can start the next day after injection of cells with physical exercises to further the treatment of urinary and/or anal incontinence according to the invention.

In another embodiment, the treatment is repeated. The treatment can be repeated e.g. within one year after the last treatment, after 10, 9, 8, 7, 6, 5, 4, 3, 2 or 1 month(s) after the last treatment or within 1 to 8 weeks, preferably 2 to 3 weeks, or 10 to 20 days after the last treatment. In particular, the treatment can be repeated within 2 to 3 weeks after the last treatment with cells from the very same cell culture as used for the prior treatment. This approach allows for a reduced injection volume per injection and gives the cells more time to adapt and to integrate and to build up the muscle. In an even more specific embodiment, the injections are repeated in time intervals of 2 to 3 weeks until an improvement of urinary and/or anal continence is achieved.

As mentioned above, a particular penetration route is through the skin of a patient in parallel to the course of the rectum. However, it is also contemplated, that the penetration can occur directly from the rectum in the vicinity of the injured muscle. In particular, the penetration and injection process is monitored via sonographic imaging means. Additionally, an alternative penetration route is contemplated for women, that is, trans-vaginal injection. In this scenario, the injection device penetrates the wall of the vagina and is moved forward until it reaches the desired injection site. In particular, the penetration and injection process is monitored by sonographic and/or EMG (electromyography) imaging means in this scenario as well.

In another embodiment, the injection comprises injecting the skeletal muscle-derived cells in form of an "injection band." "Injection band," as used herein, refers to disposition of cells along the length, or a portion of the length, of the injection track, i.e., along the canal created by insertion of the needle into the muscle tissue. In other words, following injection, the needle is withdrawn while, at the same time, cells are expelled from the syringe in a continuous or intermittent fashion with the injection needle is moved, in particular, retracted along the injection track. Such steady dispensing of cells provides for a continuous delivery of the injection solution, including cells, along the injection canal that is formed when the injection device/needle enters the target muscle-tissue. In a particular embodiment, the injection band or canal should have a diameter not bigger than about 0.8 mm, since otherwise this would lead to necrosis of the skeletal muscle-derived cells in the center of the injection canal, and consequently, result in detrimental inflammation and other processes.

The injection device for use with the methods of the present invention may be any device capable of penetrating human tissue and capable of delivering solutions, in particular solutions comprising skeletal muscle-derived cells to a desired location within the organism of a subject, in particular of a human subject. The injection device can comprise, for instance, a hollow needle. The injection device may also be any type of syringe suitable for injecting skeletal muscle-derived cells. In more sophisticated embodiments, the injection device can be for example an injection gun, injecting the cell suspension by applying air pressure. In particular, the injection device is suited for keyhole applications and keyhole surgery, respectively.

By choosing an injection needle having a particular diameter, the injection volume per mm$^3$ can be exactly pre-determined. The diameter of the injection needle will normally not exceed 5 mm, as this can lead to damage of the muscle structures.

Sonographic imaging means for monitoring the position and action of the injection device can be achieved by any standard ultrasonic imaging device known in the art. In addition to mono- or biplanar standard ultrasonic probes, also new ultrasonic technologies can be used, such as, for example, 3D-sonography or colour Doppler sonography, etc. In a particular embodiment, as discussed above, the injection device comprises a sonographic imaging means.

It is contemplated that any method or composition described herein can be implemented with respect to any other method or composition described herein.

The following examples explain the present invention but are not considered to be limiting.

Example 1—Obtaining SMDC

To obtain SMDC, a skeletal muscle biopsy was taken from M. pectoralis major or M. biceps brachii of an incontinent patient. In order to take the biopsy, first the skin was opened by an approximately 1 cm long incision above the muscle until the fascia of the M. pectoralis major was reached. After opening of the fascia, 1 cm$^3$ of muscle tissue (biopsy) was taken. The biopsy was directly transferred into a biopsy transportation medium precooled to approximately 4° C. and comprised of Ham's F10 basal medium supplemented with Gentamicin (1-5 µg/ml final concentration). The biopsy was stored for approximately 26 hours at 1-11° C. within the biopsy transportation medium. Next, the biopsy was transferred to a petri dish filled with 1×PBS. The muscle tissue was separated from connective tissue using sterile forceps and a scalpel. Then, the muscle tissue was transferred into another petri dish filled with 1×PBS and dissected into 2-3 mm$^2$ sized pieces using a scalpel. After an additional transfer step as above the tissue pieces were further cut into 1 mm pieces. The pieces finally were transferred into a centrifugation tube filled with 1×PBS and centrifuged for 10 minutes at 1300 rpm. After centrifugation the supernatant was removed and the muscle tissue resuspended in 1×PBS supplemented with 8 µg/ml Gentamicin. The muscle tissue suspension then was cooled to 2-8° C. for 48 hours. After the cooling the muscle tissue suspension was centrifuged for 10 minutes at 1300 rpm, the supernatant was then removed and 2.5 ml of a digestion solution containing 1-5 mg/ml collagenase, 2-4% v/v Hepes buffer, 0.1-10% v/v fetal calf serum and 5-10 µg/ml Gentamicin in Ham's F10. The muscle tissue suspension then was incubated for 6 to 20 hours at 37° C., 5% $CO_2$. Next, the suspension was centrifuged at 1300 rpm for 10 minutes, the supernatant was removed, the pellet resuspended in medium containing 10-20% v/v FCS, 1-3 ng/ml bFGF and 3-10 µg/ml Gentamicin in Hams F10 and plated on cell culture flasks. SMDC attached to the bottom of the culture flask were further maintained by changing medium every 3-4 days and subcultivation following detachment after confluency was reached. Subcultivation was performed until $1\times10^7$ to $5\times10^7$ SMDC were reached.

Counting of cells was carried out according to the manual of chemometec Nucleocounter™. This method uses propidiumiodid staining of nuclei and calculates the number of cells in 0.2 ml. Before automatic counting, 100 µl of a cell suspension was mixed with 200 µl of Reagent A-Lysis Buffer (in order to permeabilize the cell membrane) and incubated at room temperature for 5 minutes. Then 200 µl of Reagent B-Stabilizing Buffer was added. The suspension was mixed, collected with a Nucleocasette™ and finally measured.

Figure 1:
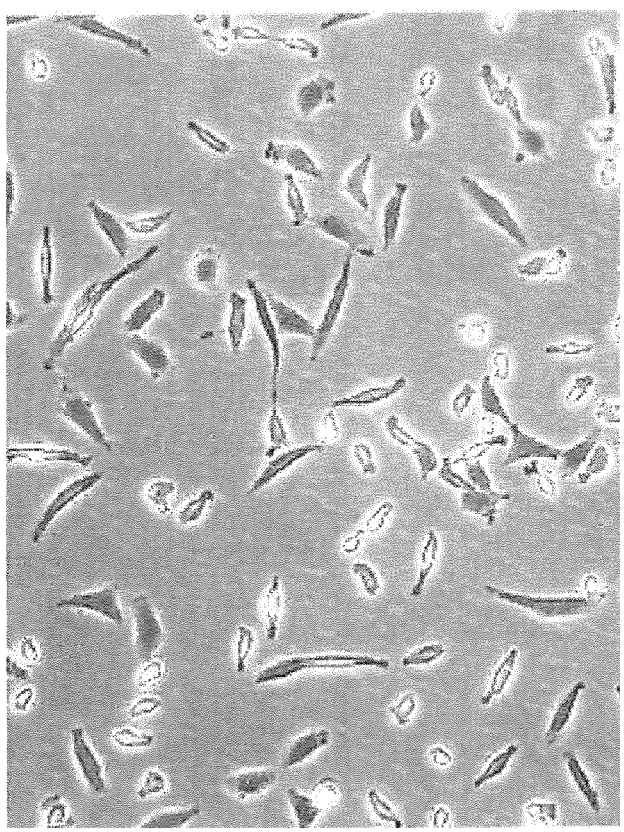

FIG. 1 demonstrates the morphology of SMDC on standard cell culture flaks obtained by the present invention visualized by phase contrast microscopy.

Example 2—Flow Cytometry

Flow cytometry analysis was performed on a Guava easyCyte 6HT 2 L flow cytometer (Merck Millipore, Darmstadt, Germany). Briefly, cells were harvested by trypsin at 37° C. for 5 min, centrifuged at 400 rcf and resuspended in 1×PBS supplemented with 1% FCS. Cells in a concentration of 40000/reaction were incubated with 5 µL anti-CD56-PE (Beckman Coulter Inc., France), Isotype IgG1-PE (Beckman Coulter), Isotype Alexa488 (Sigma), anti-CD105-PE (Beckman Coulter Inc., France) or A2B5-Alexa488 antibody (Millipore) for 15 min in a 1.5 mL Eppendorf® tube at 4° C. in dark. Cells were washed with 1 mL PBS, centrifuged at 400 rcf and resuspended in 200 µL of 1×PBS for FACS analysis in a 96 well round bottom plate. After washing and resuspension, each reaction received 5 µL of viability dye 7-aminoactinomycin D (Beckman Coulter Inc., France) and plate was incubated for 10 minutes at 4° C. Cell events were acquired with the help of Guava InCyte™ v. 2.3 software. Histograms and dot-plots were generated with a minimum of 3000 events with a sample flow rate of 1.8 µL/mL. Positive staining was obtained by comparison with Isotype control set as at least 99% negative.

Example 3—Immunocytochemistry

First, supernatant of cell culture dishes was discarded and cells washed three times with PBS. Permeabilization and fixation was carried out by covering the cells with 4% formaldehyde solution (v/v; diluted in PBS) for 20 minutes at room temperature. Then, the cells were washed with PBS three times after each conducted incubation step. Afterwards, cells were covered with 500 µl hydrogenperoxidblock (Thermo Fisher Scientific) and have been incubated for five minutes at room temperature. Primary antibodies (desmin) in a final concentration of 40 µg pro ml (w/v) were pipetted on the cells and have been incubated for at least 90 minutes (37° C., 5% $CO_2$). Cells were then covered with 500 µl biotin-conjugated secondary antibodies (goat anti rabbit, polyclonal, Thermo Fisher Scientific) and have been incubated under the same conditions as for primary antibodies but 60 minutes at least. For visualization of antibody bindings, 500 µl of horseradish streptavidin peroxidase (Vectorlabs) had to be added in a final concentration of 2-5 µg/ml (diluted in PBS) and incubated at 37° C., 5% CO2, 20 minutes long followed by covering the cells with 500 µl chromogen single-solutions, which was removed after 5 to 15 minutes. A final washing step with PBS was carried out before results could be observed. Cells stained desmin positive by immunocytochemistry are visualized in dark red color.

Example 4—Purity of SMDC

Figure 2:
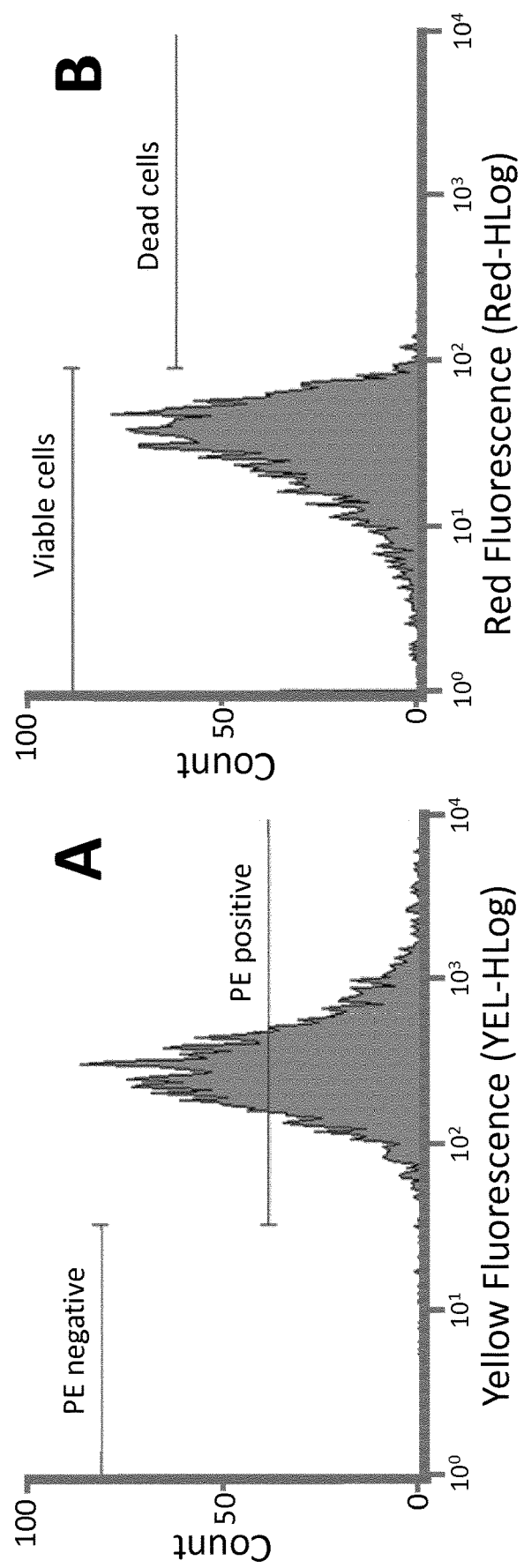
Figure 3:
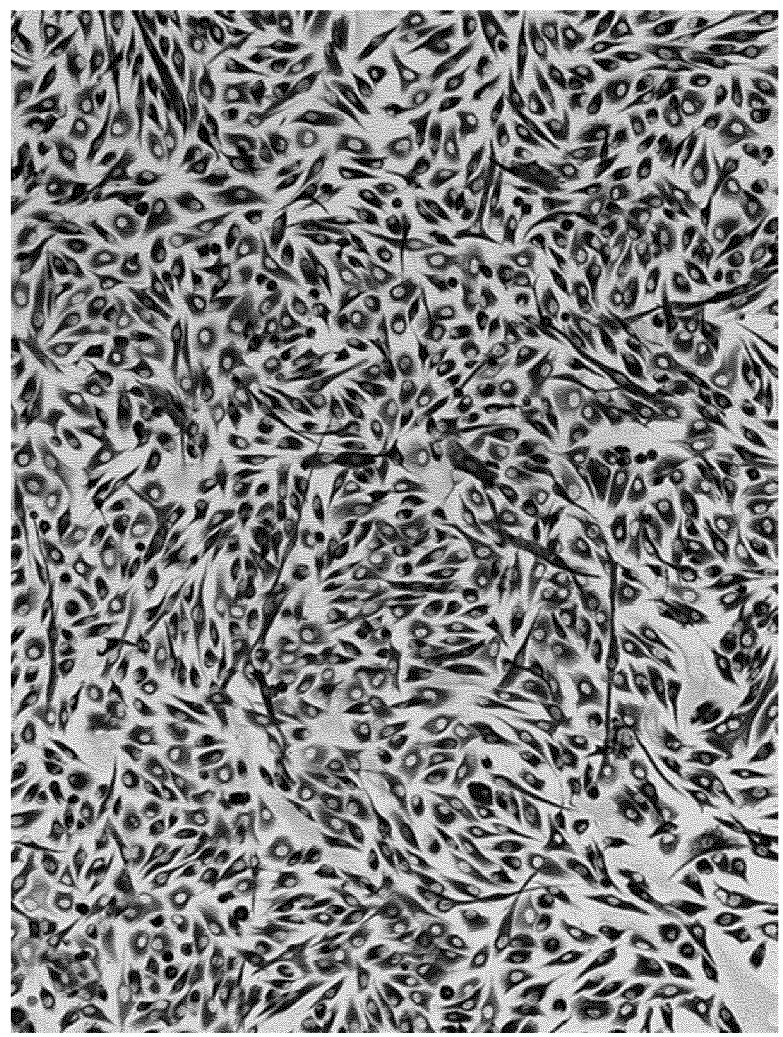
FIG. 3 shows a microscopic picture in 100× magnification of the purity of SMDC demonstrated by immunostaining for myogenic marker desmin. Positive cells appear with a darker staining, whereas negative cells are unstained.
Figure 4:
FIG. 4 shows a microscopic picture of SMDC induced to differentiate to multinucleated myotubes. Myotubes express myogenic desmin protein as shown by the dark staining.

SMDC obtained by the procedure described in Example 1 were tested for their purity of myogenic markers CD56 (NCAM) and desmin. Percent cells positive for CD56 was measured by flow cytometry as described in Example 2. SMDC obtained by the present invention as stated in Example 1 contained 99.3% CD56 positive cells (FIG. 2A) and 98.77% viable cells (FIG. 2B). Furthermore, the desmin expression of one representative SMDC batch obtained by the method described in Example 1 was analyzed by immunocytochemistry as described in Example 3. FIG. 4 demonstrates the high purity of SMDC obtained by Example 1, as most of the cells are positive for desmin staining (FIG. 3).

Example 5—Cell Differentiation

Differentiation of human myoblasts to syncytial myotubes takes place when growth medium is replaced by a serum-free differentiation medium. Skeletal Muscle Cell Differentiation Medium (Promo Cell) was supplemented with a Skeletal Muscle Cell Differentiation Medium Supplement Pack (as described in protocol of company, from which Medium has been obtained) and 250 µl of gentamycin. For the onset of differentiation, cells (in growth medium) were seeded in 4-well or 24-well dishes (60000-480000 cells) previously counted as explained in Example 1. After the cells were attached to the dish (overnight), growth media was discarded, cells were washed once with differentiation medium and covered with 500 µl differentiation medium.

Example 6—Myogenic Potency of SMDC

SMDC that are of myogenic lineage are able to fuse and form syncytial myotubes in vitro that are representative for skeletal muscle fibers in vivo. Thus myogenic potency of the SMDC was tested by in vitro differentiation. Cells obtained described in Example 1, were induced to differentiate as described in Example 5 in order to test the myogenic potency. SMDC formed huge myotubes that were desmin positive (staining as described in Example 3), as shown from a representative batch of SMDC in FIG. 4. The results confirmed the myogenic potency of SMDC which is necessary to functionally regenerate skeletal muscle tissue.

Example 7—Gene Expression Analysis

SMDC obtained by Example 1 were seeded, following cell count also described in Example 1, at a density of 500 000 cells per well in 6 well plates (NUNC Thermo Scientific) until 70 percent confluency, then total RNA was isolated using RNeasy RNA isolation kit (QIAGEN) according to the manufacturers instruction. The RNA concentration and purity was assessed by microfluid analysis using denaturing gel electrophoresis and the 2100 Agilent bioanalyzer. Sample preparation for microarray hybridization was carried out as described in the NuGEN Ovation PicoSL WTA System V2 and NUGEN Encore Biotin Module manuals (NuGEN Technologies, Inc, San Carlos, Calif., USA). In brief, 7.5 ng of total RNA was reverse transcribed into double-stranded cDNA in a two-step process, introducing a SPIA tag sequence. Bead purified cDNA was amplified by a SPIA amplification reaction followed by an additional bead purification. 4.5 µg of SPIA cDNA was fragmented, terminally biotin-labeled and hybridized to Affymetrix PrimeView Human Gene Expression arrays for 16 h at 45° C. in a GeneChip hybridization oven 640. Hybridized arrays were washed and stained in an Affymetrix Fluidics Station FS450, and the fluorescent signals were measured with an Affymetrix GeneChip Scanner 3000 7G. Fluidics and scan functions were controlled by the Affymetrix GeneChip Command Console v4.1.3 software. Sample processing was performed at an Affymetrix Service Provider and Core Facility, "KFB—Center of Excellence for Fluorescent Bioanalytics" (Regensburg, Germany; www.kfb-regensburg.de). Summarized probe set signals in log 2 scale were calculated by using the RMA (1) algorithm with the Affymetrix GeneChip Expression Console v1.4 Software. In order to compare gene expression results of SMDC obtained by Example 1 with SMDC obtained by state of the art methods, gene expression data of commercially available SMDC (Lonza) published by Abujarour et al., 2014 (R. Abujarour et al., "Myogenic differentiation of muscular dystrophy-specific induced pluripotent stem cells for use in drug discovery," Stem Cells Transl. Med, vol. 3, no. 2, pp. 149-160, February 2014) was downloaded from a database attached to a publication (ftp://ftp.ncbi.nlm.nih.gov/pub/geo/DATA/supplementary/series/GSE46633/ GSE46633_RAW.tar; last accession 21.07.2017). Comparison of gene expression of SMDC obtained by Example 1 with SMDC analyzed by Abujarour et al., 2014 was performed by comparing the average reads per annotation of different genes by applying Partek Flow software according to the providing company (Partek Inc.). Higher average reads per annotation thus represent a higher abundance of the annotated mRNA standing for a higher gene expression.

Example 8—Neuromuscular Support Features of SMDC

Neuromuscular support feature of SMDC obtained by employing Example 1 was determined by positive binding of A2B5 antibody to the cell surface of SMDC as performed by flow cytometry (described in Example 2). As it is shown in FIG. 5, 96.16% of SMDC obtained by Example 1 are positive for A2B5 reactive antibody, demonstrating that besides their myogenic commitment (desmin, CD56 expression), SMDC also exhibit neuronal characteristics. To compare the neuromuscular support feature of SMDC obtained by the present invention with myoblast isolated by state of the art methods, the gene expression of enzymes essential for the formation of A2B5 reactive gangliosides exhibiting highest glycosphingolipid acceptor activity in vitro ST3GAL1 and ST3GAL2 of SMDC was analyzed as stated in Example 7. Both ST3GAL1 and ST3GAL2 mRNA expression was higher in SMDC obtained by the herein proposed invention compared to commercially available SMDC as shown in FIG. 5. Furthermore, also ST3GAL3 expression was higher in SMDC obtained by Example 1.

Example 9—Obtaining Cells Without Cooling After Tissue Dissection

As a comparative example, the method of the present invention has been conducted by omitting the cooling step. To obtain SMDC, a skeletal muscle biopsy was taken from M. pectoralis major or M. biceps brachii of an incontinent patient. In order to take the biopsy, first the skin was opened by an approximately 1 cm long incision above the muscle until the fascia of the M. pectoralis major was reached. After opening of the fascia, 1 cm$^3$ of muscle tissue (biopsy) was taken. The biopsy was directly transferred into a biopsy transportation medium precooled to approximately 4° C. and comprised of Ham's F10 basal medium supplemented with Gentamicin (1-5 µg/ml final concentration). The biopsy was stored for approximately 26 hours at 1-11° C. within the biopsy transportation medium. Next, the biopsy was transferred to a petri dish filled with 1×PBS. The muscle tissue was separated from connective tissue using sterile forceps and a scalpel. Then, the muscle tissue was transferred into another petri dish filled with 1×PBS and dissected into 2-3 mm$^2$ sized pieces using a scalpel. After an additional transfer step as above the tissue pieces were further cut into 1 mm pieces. The pieces finally were transferred into a centrifugation tube filled with 1×PBS and centrifuged for 10 minutes at 1300 rpm. After centrifugation the supernatant was removed and the muscle tissue resuspended in 1×PBS supplemented with 8 µg/ml Gentamicin. The muscle tissue suspension was centrifuged for 10 minutes at 1300 rpm, the supernatant was then removed and 2.5 ml of a digestion solution containing 1-5 mg/ml collagenase, 2-4% v/v Hepes buffer, 0.1-10% v/v fetal calf serum and 5-10 µg/ml Gentamicin in Ham's F10. The muscle tissue suspension then was incubated for 6 to 20 hours at 37° C., 5% $CO_2$. Next, the suspension was centrifuged at 1300 rpm for 10 minutes, the supernatant was removed, the pellet resuspended in medium containing 10-20% v/v FCS, 1-3 ng/ml bFGF and 3-10 µg/ml Gentamicin in Hams F10 and plated on cell culture flasks. SMDC attached to the bottom of the culture flask were further maintained by changing medium every 3-4 days and subcultivation following detachment after confluency was reached. Subcultivation was performed until $1 \times 10^7$ to $5 \times 10^7$ SMDC were reached.

Example 10—Mesenchymal Cell Marker Expression of SMDC

Mesenchymal marker expression of SMDC obtained by employing Example 1 was determined by binding of anti-CD105 antibody, anti-CD105-PE (Beckman Coulter Inc., France), to the cell surface of SMDC measured by flow cytometry (described in Example 2). As it is shown in FIG. 8, 98.69% of SMDC obtained by Example 1 are detected as positive for CD105 reactive antibody when threshold for positivity was set according to Isotype control (0.31% positive), suggesting that SMDC are mesenchymal cells and/or of mesenchymal origin.

Example 11—Acetylcholinesterase Activity Measurement of SMDC

For measurement of Acetylcholinesterase (AChE) activity, 200 000 SMDC were seeded in a gelatin coated well of a 24-well plate and induced to differentiate as explained in Example 5. Six days after onset of differentiation, differentiation medium was carefully removed from 24-well plate with the immediate addition of 300 µL 0.5 mM 5,5'-dithiobis-2-nitrobenzoic acid (DTNB) solution (prepared in phosphate buffer, pH 7.2 with 0.1% triton X-100). After 2 minutes of incubation at room temperature in dark, 50 µL of 5.76 mM Acetylthiocholine iodide (ATI) (prepared in distil water) was added. The reaction contents were incubated for 60 minutes at 30° C. in dark followed by the optical density (OD) measurement at 412 nm (OD412 nm) on an Anthos Zenyth 340rt microplate reader (Biochrom Ltd., Cambridge, UK). A blank reaction was also included, which was composed of all reagents except cells. Corrected OD412 nm values were obtained by subtracting blank mean measurement from mean OD412 nm. AChE activity in relative mU (AChE mUrel) was calculated according to the straight line equation of a standard curve. Standard curve was obtained by measuring 4-500 mU/ml dilutions of a ready to use 50 U/mL AChE stock (from Electrophorus electricus, AAT Bioquest® Inc., Sunnyvale, Calif., USA). Standard dilutions were prepared in phosphate buffer (pH 7.2 with 0.1% triton X-100) and were immediately used. For AChE standard enzyme analysis, 200 µL of each dilution was mixed with 300 µL of 0.5 mM DTNB and 50 µL of 5.76 mM ATI, respectively and the OD412 nm was measured after 60 minutes in a 24-well plate. In order to normalize for cell type specific protein concentrations, AChE activity of measured amount of cells was divided by the total protein content of these cells resulting in mUrel AChE activity per g protein (AChE mUrel/g protein). In order to analyze the total amount of protein within a cell population, an aliquot of adherent cells differentiated according to Example 5 were first washed twice with PBS, subsequently covered with PBST (0.1% Triton X-100) and then incubated for 10 minutes at room temperature. Next, the lysate was resuspended and transferred to an Eppendorf® tube, shortly vortexed and then centrifuged for 4 minutes at 1200*g. Finally, the clear supernatant was transferred into a fresh Eppendorf tube and the protein concentration was determined using the Pierce BCA Protein Assay Kit (Thermo Scientific, MA, USA) according to the manufacturer's instructions by measuring the OD at 540 nm with an Anthos Zenyth 340rt microplate reader (Biochrom Ltd., Cambridge, UK).

Example 12—Quantification of SMDC Fusion Competency

Fusion competency of SMDC is based on their ability to form multinucleated myotubes and represents their myogenic potency. Fusion competency is quantified as fusion index, which represents the number of nuclei located within multinucleated myotubes, defined as cells containing at least 3 nuclei, divided by the total number of nuclei in the observed microscopic field. In order to determine the fusion index of SMDC, 2*105 cells were seeded onto gelatin coated 24-well plates and induced to differentiate by switching from growth to skeletal muscle differentiation medium 24 hours after seeding. After 6 days of differentiation, cells were washed twice with PBS and fixed with 4% PFA for 10 minutes. Next, cells were washed three times with PBS and stained by 2 µg/mL Hoechst33342 solution for 20 minutes. For each sample at least three fields were captured during immunofluorescence imaging and overlaid with phase-contrast images to allow easy detection of nuclei and cell boundaries. Fusion index was calculated for each captured field of vision by dividing the number of nuclei within tubes with the total number of nuclei per field following calculation of the mean for all analyzed fields. Only cells that have at least 3 nuclei were considered as myotubes. For statistical analysis at least 3 populations derived from different patients were analyzed for each group cells.

The invention claimed is:

1. A method of treating incontinence comprising administering a skeletal muscle derived cell population comprising at least 60% CD56 positive and 60% A2B5 positive cells to a subject in need thereof, wherein the skeletal muscle derived cell (SMDC) population is obtained according to the method comprising the steps of:
   (a) cooling of a sample obtained from skeletal muscle tissue in a buffer;
   (b) processing followed by cooling of the sample, wherein cooling is conducted at a temperature of 1 to 16° C. for a time in the range of 2 to 48 hours;
   (c) resuspending the sample of step (b) in medium with serum comprising at least one enzyme and heating up to 38° C. for 1 to 20 hours; pelleting the sample and
   (d) resuspending the pellet of the sample of step (c) to provide a single cell suspension from the sample of step (c), thereby obtaining SMDCs.

2. The method according to claim 1, wherein the incontinence is fecal incontinence and/or urinary incontinence.

3. The method according to claim 1, wherein the incontinence is anal incontinence.

4. The method according to claim 1, wherein the SMDC population is characterized by the expression of distinct marker combinations selected from the positive expression of at least one or more of the markers selected from CD56, A2B5, CD105, Myf5, and Pax7, and the negative expression of at least one or more of the markers selected from CD34, and MyoD.

5. The method according to claim 1, wherein step (a) is conducted at a temperature lower than 16° C., and for a time in the range of up to 96 hours.

6. The method according to claim 1, wherein step (b) comprises the use of scissors, scalpel, tweezers, filter, or ball mill.

7. The method according to claim 1, wherein the cooling in step (b) is conducted at a temperature in the range of 4 to 8° C., and for a time in the range of 2 hours to 48 hours.

8. The method according to claim 1, step (c) comprises conducting the enzymatically treating with a solution comprising any one or more selected from the group consisting of trypsin, papain, elastase, hyaluronidase, collagenase, deoxyribonuclease, and DNAse.

9. The method according to claim 1, wherein step (c) is conducted at a temperature in the range of 25 to 38° C.

10. The method according to claim 1, wherein step (d) further comprises sorting the SMDCs according to a method selected from at least one of FACS sorting, centrifugation, electrokinetic sorting, acoustophoresis sorting, bead-based cell sorting, and optical sorting.

11. The method according to claim 1, wherein a further step (e) is conducted after step (d) including incubating of the single cell suspension obtained in step (d), wherein the incubation in step (e) is conducted at a temperature in the range of 25 to 38° C., thereby obtaining adherent SMDCs.

12. The method according to claim 1, wherein after step (e) a further step (f) is conducted comprising discarding of non-adherent cells of step (e), wherein step (f) is preferably conducted after at least 6 hours to 4 days.

13. The method according to claim 1, wherein after step (f) a further step (g) is conducted of propagating of the adherent cells of step (e), the propagating in step (h) comprises culturing of the adherent cells for 1 to 5 passages to 70 to 80% confluency.

* * * * *